US009512443B2

(12) United States Patent
Richmond et al.

(10) Patent No.: US 9,512,443 B2
(45) Date of Patent: Dec. 6, 2016

(54) RECOMBINANT EXPRESSION OF MULTIPROTEIN COMPLEXES USING POLYGENES

(75) Inventors: Timothy Richmond, Zurich (CH); Imre Berger, Saint-Egrève (FR)

(73) Assignee: ETH ZURICH, Zurich (CH)

( * ) Notice: Subject to any disclaimer, the term of this patent is extended or adjusted under 35 U.S.C. 154(b) by 1872 days.

(21) Appl. No.: 12/084,649

(22) PCT Filed: Nov. 6, 2006

(86) PCT No.: PCT/EP2006/010608

§ 371 (c)(1), (2), (4) Date: May 7, 2008

(87) PCT Pub. No.: WO2007/054250

PCT Pub. Date: May 18, 2007

(65) Prior Publication Data

US 2009/0222936 A1 Sep. 3, 2009

(30) Foreign Application Priority Data

Nov. 8, 2005 (EP) .................................... 05024271

(51) Int. Cl.

| | |
|---|---|
| ***C12N 15/63*** | (2006.01) |
| ***C12N 15/85*** | (2006.01) |
| ***C12N 5/10*** | (2006.01) |
| ***C07K 14/47*** | (2006.01) |

(52) U.S. Cl.

CPC ........... *C12N 15/85* (2013.01); *C07K 14/4702* (2013.01); *C07K 2319/21* (2013.01); *C07K 2319/50* (2013.01); *C12N 2799/026* (2013.01)

(58) Field of Classification Search

CPC ...... C12N 15/63; C12N 15/66; C12N 15/79; C12N 15/85; C12N 2330/51; C12N 2510/00; C12N 2830/20; C12N 2840/20; C07K 2319/50

USPC .............................................. 435/320.1, 325

See application file for complete search history.

(56) References Cited

U.S. PATENT DOCUMENTS

| | | | | |
|---|---|---|---|---|
| 5,162,601 | A * | 11/1992 | Slightom | 800/301 |
| 2003/0203447 | A1 * | 10/2003 | Horwitz | 435/69.1 |
| 2004/0235011 | A1 | 11/2004 | Cooper et al. | |

FOREIGN PATENT DOCUMENTS

| | | | |
|---|---|---|---|
| WO | 2005/085456 | | 9/2005 |
| WO | WO 2005/085426 | * | 9/2005 |

OTHER PUBLICATIONS

Szymczak et al. (2004) Nat. Biotech., vol. 22(5) 589-594.*

International Search Report issued Mar. 26, 2007 in the International (PCT) Application of which the present application is the U.S. National Stage.

A. L. Szymczak et al., "Correction of Multi-Gene Deficiency in vivo using a Single 'Self-Cleaving' 2A Peptide-Based Retroviral Vector", Nature Biotechnology, vol. 22, No. 5, pp. 589-594, May 2004.

J. Fang et al., "Stable Antibody Expression at Therapeutic Levels Using the 2A Peptide", Nature Biotechnology, vol. 23, No. 5, pp. 584-590, May 2005.

M. J. Osborn et al., "A Picornaviral 2A-Like Sequence-Based Tricistronic Vector Allowing for High-Level Therapeutic Gene Expression Coupled to a Dual-Reporter System", Molecular Therapy, vol. 12, No. 3, pp. 569-574, Sep. 2005.

P. de Felipe, "Skipping the Co-Expression Problem: The New 2A "CHYSEL" Technology", Genetic Vaccines and Therapy, vol. 2, No. 13, pp. 1-6, Sep. 13, 2004.

D. J. Fitzgerald et al., "Protein Complex Expression by Using Multigene Baculoviral Vectors", Nature Methods, vol. 3, No. 12, pp. 1021-1032, Dec. 2006.

* cited by examiner

*Primary Examiner* — Anne Marie S Wehbe

(74) *Attorney, Agent, or Firm* — Wenderoth, Lind & Ponack, L.L.P.

(57) ABSTRACT

The present invention relates to a recombinant polynucleotide encoding a polygene coding for at least three polypeptides wherein at least one of the genes constituting the polygene is of non-viral origin, at least two of the polypeptides encoded by the genes constituting the polygene are each capable of at least transiently interacting with at least one other polypeptide encoded by a gene of said polygene, and the genes constituting the polygene are each connected to one mother by a sequence coding for at least one protease cleavage site. The present invention also relates to polyproteins encoded by the polygene. Further embodiments of the present invention are a vector containing the recombinant polypeptide, a host cell containing the recombinant polypeptide and/or the vector and a non-human transgenic animal transformed with the recombinant polypeptide and/or the vector. The present invention also relates to methods for the production of the polynucleotide and for the manufacture of multiprotein complexes. The embodiments of the present invention are particularly useful in gene therapy, drug candidate screening, vaccine production and crystallization of multiprotein complexes for structural investigations.

5 Claims, 17 Drawing Sheets

Fig. 1

```
Universal code
Total amino acid number: 819, MW=91858
Max ORF starts at AA pos 541(may be DNA pos 1623) for 286 AA(858
bases), MW=32543
AAseq:
                                                          RsrII
1                                                CGAATTCCTCGAGCGGT
1                                                                R

61      CCGGAGGTAACGGATCCGAAAACCTGTATTTTCAGGGTTCTGGGATTGTACCGCAGCTGC
20      S  G  G  N  G  S  E  N  L  Y  F  Q  G  S  G  I  V  P  Q  L

121     AAAATATTGTATCCACAGTGAATCTTGGTTGTAAACTTGACCTAAAGACCATTGCACTTC
40      Q  N  I  V  S  T  V  N  L  G  C  K  L  D  L  K  T  I  A  L

181     GTGCCCGAAACGCCGAATATAATCCCAAGCGGTTTGCTGCGGTAATCATGAGGATAAGAG
60      R  A  R  N  A  E  Y  N  P  K  R  F  A  A  V  I  M  R  I  R

241     AGCCACGAACCACGGCACTGATTTTCAGTTCTGGGAAAATGGTGTGCACAGGAGCCAAGA
80      E  P  R  T  T  A  L  I  F  S  S  G  K  M  V  C  T  G  A  K

301     GTGAAGAACAGTCCAGACTGGCAGCAAGAAAATATGCTAGAGTTGTACAGAAGTTGGGTT
100     S  E  E  Q  S  R  L  A  A  R  K  Y  A  R  V  V  Q  K  L  G

361     TTCCAGCTAAGTTCTTGGACTTCAAGATTCAGAACATGGTGGGGAGCTGTGATGTGAAGT
120     F  P  A  K  F  L  D  F  K  I  Q  N  M  V  G  S  C  D  V  K

421     TTCCTATAAGGTTAGAAGGCCTTGTGCTCACCCACCAACAATTTAGTAGTTATGAGCCAG
140     F  P  I  R  L  E  G  L  V  L  T  H  Q  Q  F  S  S  Y  E  P

481     AGTTATTTCCTGGTTTAATCTACAGAATGATCAAACCCAGAATTGTTCTCCTTATTTTTG
160     E  L  F  P  G  L  I  Y  R  M  I  K  P  R  I  V  L  L  I  F

541     TTTCTGGAAAAGTTGTATTAACAGGTGCTAAAGTCAGAGCAGAAATTTATGAAGCATTTG
180     V  S  G  K  V  V  L  T  G  A  K  V  R  A  E  I  Y  E  A  F

                                              RsrII
601     AAAACATCTACCCTATTCTAAAGGGATTCAGGAAGACGACGCGGTCCGGC
200     E  N  I  Y  P  I  L  K  G  F  R  K  T  T  R
```

Fig. 8

```
SEQ  pFBDO[hTBPc]3: 6959 bp;
Composition  1827 A; 1609 C; 1674 G; 1849 T; 0 OTHER
Percentage:  26.3% A; 23.1% C; 24.1% G; 26.6% T; 0.0%OTHER
Molecular Weight (kDa): ssDNA: 2149.69 dsDNA: 4290.03
KEYWORD     CIRCULAR

ORIGIN
1       TTCTCTGTCA CAGAATGAAA ATTTTTCTGT CATCTCTTCG TTATTAATGT TTGTAATTGA
61      CTGAATATCA ACGCTTATTT GCAGCCTGAA TGGCGAATGG GACGCGCCCT GTAGCGGCGC
121     ATTAAGCGCG GCGGGTGTGG TGGTTACGCG CAGCGTGACC GCTACACTTG CCAGCGCCCT
181     AGCGCCCGCT CCTTTCGCTT TCTTCCCTTC CTTTCTCGCC ACGTTCGCCG GCTTTCCCCG
241     TCAAGCTCTA AATCGGGGGC TCCCTTTAGG GTTCCGATTT AGTGCTTTAC GGCACCTCGA
301     CCCCAAAAAA CTTGATTAGG GTGATGGTTC ACGTAGTGGG CCATCGCCCT GATAGACGGT
361     TTTTCGCCCT TTGACGTTGG AGTCCACGTT CTTTAATAGT GGACTCTTGT TCCAAACTGG
421     AACAACACTC AACCCTATCT CGGTCTATTC TTTTGATTTA TAAGGGATTT TGCCGATTTC
481     GGCCTATTGG TTAAAAAATG AGCTGATTTA ACAAAAATTT AACGCGAATT TTAACAAAAT
541     ATTAACGTTT ACAATTTCAG GTGGCACTTT TCGGGGAAAT GTGCGCGGAA CCCCTATTTG
601     TTTATTTTTC TAAATACATT CAAATATGTA TCCGCTCATG AGACAATAAC CCTGATAAAT
661     GCTTCAATAA TATTGAAAAA GGAAGAGTAT GAGTATTCAA CATTTCCGTG TCGCCCTTAT
721     TCCCTTTTTT GCGGCATTTT GCCTTCCTGT TTTTGCTCAC CCAGAAACGC TGGTGAAAGT
781     AAAAGATGCT GAAGATCAGT TGGGTGCACG AGTGGGTTAC ATCGAACTGG ATCTCAACAG
841     CGGTAAGATC CTTGAGAGTT TTCGCCCCGA AGAACGTTTT CCAATGATGA GCACTTTTAA
901     AGTTCTGCTA TGTGGCGCGG TATTATCCCG TATTGACGCC GGGCAAGAGC AACTCGGTCG
961     CCGCATACAC TATTCTCAGA ATGACTTGGT TGAGTACTCA CCAGTCACAG AAAAGCATCT
1021    TACGGATGGC ATGACAGTAA GAGAATTATG CAGTGCTGCC ATAACCATGA GTGATAACAC
1081    TGCGGCCAAC TTACTTCTGA CAACGATCGG AGGACCGAAG GAGCTAACCG CTTTTTTGCA
1141    CAACATGGGG GATCATGTAA CTCGCCTTGA TCGTTGGGAA CCGGAGCTGA ATGAAGCCAT
1201    ACCAAACGAC GAGCGTGACA CCACGATGCC TGTAGCAATG GCAACAACGT TGCGCAAACT
1261    ATTAACTGGC GAACTACTTA CTCTAGCTTC CCGGCAACAA TTAATAGACT GGATGGAGGC
1321    GGATAAAGTT GCAGGACCAC TTCTGCGCTC GGCCCTTCCG GCTGGCTGGT TTATTGCTGA
1381    TAAATCTGGA GCCGGTGAGC GTGGGTCTCG CGGTATCATT GCAGCACTGG GGCCAGATGG
1441    TAAGCCCTCC CGTATCGTAG TTATCTACAC GACGGGGAGT CAGGCAACTA TGGATGAACG
1501    AAATAGACAG ATCGCTGAGA TAGGTGCCTC ACTGATTAAG CATTGGTAAC TGTCAGACCA
1561    AGTTTACTCA TATATACTTT AGATTGATTT AAAACTTCAT TTTTAATTTA AAAGGATCTA
1621    GGTGAAGATC CTTTTTGATA ATCTCATGAC CAAAATCCCT TAACGTGAGT TTTCGTTCCA
1681    CGTAATCTGC TGCTTGCAAA CAAAAAAACC ACCGCTACCA GCGGTGGTTT GTTTGCCGGA
1741    TCAAGAGCTA CCAACTCTTT TTCCGAAGGT AACTGGCTTC AGCAGAGCGC AGATACCAAA
1801    TACTGTCCTT CTAGTGTAGC CGTAGTTAGG CCACCACTTC AAGAACTCTG TAGCACCGCC
1861    TACATACCTC GCTCTGCTAA TCCTGTTACC AGTGGCTGCT GCCAGTGGCG ATAAGTCGTG
1921    TCTTACCGGG TTGGACTCAA GACGATAGTT ACCGGATAAG GCGCAGCGGT CGGGCTGAAC
1981    GGGGGGTTCG TGCACACAGC CCAGCTTGGA GCGAACGACC TACACCGAAC TGAGATACCT
2041    ACAGCGTGAG CATTGAGAAA GCGCCACGCT TCCCGAAGGG AGAAAGGCGG ACAGGTATCC
2101    GGTAAGCGGC AGGGTCGGAA CAGGAGAGCG CACGAGGGAG CTTCCAGGGG GAAACGCCTG
2161    GTATCTTTAT AGTCCTGTCG GGTTTCGCCA CCTCTGACTT GAGCGTCGAT TTTTGTGATG
2221    CTCGTCAGGG GGGCGGAGCC TATGGAAAAA CGCCAGCAAC GCGGCCTTTT TACGGTTCCT
2281    GGCCTTTTGC TGGCCTTTTG CTCACATGTT CTTTCCTGCG TTATCCCCTG ATTCTGTGGA
2341    TAACCGTATT ACCGCCTTTG AGTGAGCTGA TACCGCTCGC CGCAGCCGAA CGACCGAGCG
2401    CAGCGAGTCA GTGAGCGAGG AAGCGGAAGA GCGCCTGATG CGGTATTTTC TCCTTACGCA
2461    TCTGTGCGGT ATTTCACACC GCAGACCAGC CGCGTAACCT GGCAAAATCG GTTACGGTTG
2521    AGTAATAAAT GGATGCCCTG CGTAAGCGGG TGTGGGCGGA CAATAAAGTC TTAAACTGAA
2581    CAAAATAGAT CTAAACTATG ACAATAAAGT CTTAAACTAG ACAGAATAGT TGTAAACTGA
2641    AATCAGTCCA GTTATGCTGT GAAAAAGCAT ACTGGACTTT TGTTATGGCT AAAGCAAACT
2701    CTTCATTTTC TGAAGTGCAA ATTGCCCGTC GTATTAAAGA GGGGCGTGGC CAAGGGCATG
2761    GTAAAGACTA TATTCGCGGC GTTGTGACAA TTTACCGAAC AACTCCGCGG CCGGGAAGCC
2821    GATCTCGGCT TGAACGAATT GTTAGGTGGC GGTACTTGGG TCGATATCAA AGTGCATCAC
```

Fig. 8 (cont'd)

```
2881  TTCTTCCCGT ATGCCCAACT TTGTATAGAG AGCCACTGCG GGATCGTCAC CGTAATCTGC
2941  TTGCACGTAG ATCACATAAG CACCAAGCGC GTTGGCCTCA TGCTTGAGGA GATTGATGAG
3001  CGCGGTGGCA ATGCCCTGCC TCCGGTGCTC GCCGGAGACT GCGAGATCAT AGATATAGAT
3061  CTCACTACGC GGCTGCTCAA ACCTGGGCAG AACGTAAGCC GCGAGAGCGC CAACAACCGC
3121  TTCTTGGTCG AAGGCAGCAA GCGCGATGAA TGTCTTACTA CGGAGCAAGT TCCCGAGGTA
3181  ATCGGAGTCC GGCTGATGTT GGGAGTAGGT GGCTACGTCT CCGAACTCAC GACCGAAAAG
3241  ATCAAGAGCA GCCCGCATGG ATTTGACTTG GTCAGGGCCG AGCCTACATG TGCGAATGAT
3301  GCCCATACTT GAGCCACCTA ACTTTGTTTT AGGGCGACTG CCCTGCTGCG TAACATCGTT
3361  CTTGCTGCTT GGATGCCCGA GGCATAGACT GTACAAAAAA ACAGTCATAA CAAGCCATGA
3421  AAACCGCCAC TGCGCCGTTA CCACCGCTGC GTTCGGTCAA GGTTCTGGAC CAGTTGCGTG
3481  AGCGCATACG CTACTTGCAT TACAGTTTAC GAACCGAACA GGCTTATGTC AACTGGGTTC
3541  GTGCCTTCAT CCGTTTCCAC GGTGTGCGTC ACCCGGCAAC CTTGGGCAGC AGCGAAGTCG
3601  AGGCATTTCT GTCCTGGCTG GCGAACGAGC GCAAGGTTTC GGTCTCCACG CATCGTCAGG
3661  CATTGGCGGC CTTGCTGTTC TTCTACGGCA AGGTGCTGTG CACGGATCTG CCCTGGCTTC
3721  AGGAGATCGG TAGACCTCGG CCGTCGCGGC GCTTGCCGGT GGTGCTGACC CCGGATGAAG
3781  TGGTTCGCAT CCTCGGTTTT CTGGAAGGCG AGCATCGTTT GTTCGCCCAG GACTCTAGCT
3841  ATAGTTCTAG TGGTTGGCCT ACAGCTTTGT TTAAACAAAG CTGTACCCGT AGTGGCTATG
3901  GCAGGGCTTG CCGCCCCGAC GTTGGCTGCG AGCCCTGGGC CTTCACCCGA ACTTGGGGGT
3961  TGGGGTGGGG AAAAGGAAGA AACGCGGGCG TATTGGTCCC AATGGGGTCT CGGTGGGGTA
4021  TCGACAGAGT GCCAGCCCTG GGACCGAACC CCGCGTTTAT GAACAAACGA CCCAACACCC
4081  GTGCGTTTTA TTCTGTCTTT TTATTGCCGT CATAGCGCGG GTTCCTTCCG GTATTGTCTC
4141  CTTCCGTGTT TCAGTTAGCC TCCCCCATCT CCCGGTACCG CATGCTATGC ATCAGCTGCT
4201  AGCACCATGG CTCGAGATCC CGGGTGATCA AGTCTTCGTC GAGTGATTGT AAATAAAATG
4261  TAATTTACAG TATAGTATTT TAATTAATAT ACAAATGATT TGATAATAAT TCTTATTTAA
4321  CTATAATATA TTGTGTTGGG TTGAATTAAA GGTCCGTATA CTAGTATCGA TTCGCGACCT
4381  ACTCCGGAAT ATTAATAGAT CATGGAGATA ATTAAAATGA TAACCATCTC GCAAATAAAT
4441  AAGTATTTTA CTGTTTTCGT AACAGTTTTG TAATAAAAAA ACCTATAAAT ATTCCGGATT
4501  ATTCATACCG TCCCACCATC GGGCGCGGAT CCTCGAGATG GGTAACCATG ACAAGCGACG
4561  ATGGAAAAAG AATTTCATAG CCGTCTCAGC AGCCAACCGC TTTAAGAAAA TCTCATCCTC
4621  CGGGGCAGCT AGCTGGAGCC ACCCGCAGTT CGAAAAAGGC GCCGACGACG ACGACGACAA
4681  GGGCTCCCAT ATGTCTGGGA TTGTACCGCA GCTGCAAAAT ATTGTATCCA CAGTGAATCT
4741  TGGTTGTAAA CTTGACCTAA AGACCATTGC ACTTCGTGCC CGAAACGCCG AATATAATCC
4801  CAAGCGGTTT GCTGCGGTAA TCATGAGGAT AAGAGAGCCA CGAACCACGG CACTGATTTT
4861  CAGTTCTGGG AAAATGGTGT GCACAGGAGC CAAGAGTGAA GAACAGTCCA GACTGGCAGC
4921  AAGAAAATAT GCTAGAGTTG TACAGAAGTT GGGTTTTCCA GCTAAGTTCT TGGACTTCAA
4981  GATTCAGAAC ATGGTGGGGA GCTGTGATGT GAAGTTTCCT ATAAGGTTAG AAGGCCTTGT
5041  GCTCACCCAC CAACAATTTA GTAGTTATGA GCCAGAGTTA TTTCCTGGTT TAATCTACAG
5101  AATGATCAAA CCCAGAATTG TTCTCCTTAT TTTTGTTTCT GGAAAAGTTG TATTAACAGG
5161  TGCTAAAGTC AGAGCAGAAA TTTATGAAGC ATTTGAAAAC ATCTACCCTA TTCTAAAGGG
5221  ATTCAGGAAG ACGACGCGGT CCGGAGGTAA CGGATCCGAA AACCTGTATT TTCAGGGTTC
5281  TGGGATTGTA CCGCAGCTGC AAAATATTGT ATCCACAGTG AATCTTGGTT GTAAACTTGA
5341  CCTAAAGACC ATTGCACTTC GTGCCCGAAA CGCCGAATAT AATCCCAAGC GGTTTGCTGC
5401  GGTAATCATG AGGATAAGAG AGCCACGAAC CACGGCACTG ATTTTCAGTT CTGGGAAAAT
5461  GGTGTGCACA GGAGCCAAGA GTGAAGAACA GTCCAGACTG GCAGCAAGAA AATATGCTAG
5521  AGTTGTACAG AAGTTGGGTT TTCCAGCTAA GTTCTTGGAC TTCAAGATTC AGAACATGGT
5581  GGGGAGCTGT GATGTGAAGT TTCCTATAAG GTTAGAAGGC CTTGTGCTCA CCCACCAACA
5641  ATTTAGTAGT TATGAGCCAG AGTTATTTCC TGGTTTAATC TACAGAATGA TCAAACCCAG
5701  AATTGTTCTC CTTATTTTTG TTTCTGGAAA AGTTGTATTA ACAGGTGCTA AAGTCAGAGC
5761  AGAAATTTAT GAAGCATTTG AAAACATCTA CCCTATTCTA AAGGGATTCA GGAAGACGAC
5821  GCGGTCCGGA GGTAACGGAT CCGAAAACCT GTATTTTCAG GGTTCTGGGA TTGTACCGCA
5881  GCTGCAAAAT ATTGTATCCA CAGTGAATCT TGGTTGTAAA CTTGACCTAA AGACCATTGC
5941  ACTTCGTGCC CGAAACGCCG AATATAATCC CAAGCGGTTT GCTGCGGTAA TCATGAGGAT
6001  AAGAGAGCCA CGAACCACGG CACTGATTTT CAGTTCTGGG AAAATGGTGT GCACAGGAGC
6061  CAAGAGTGAA GAACAGTCCA GACTGGCAGC AAGAAAATAT GCTAGAGTTG TACAGAAGTT
6121  GGGTTTTCCA GCTAAGTTCT TGGACTTCAA GATTCAGAAC ATGGTGGGGA GCTGTGATGT
```

Fig. 8 (cont'd)

```
6181   GAAGTTTCCT ATAAGGTTAG AAGGCCTTGT GCTCACCCAC CAACAATTTA GTAGTTATGA
6241   GCCAGAGTTA TTTCCTGGTT TAATCTACAG AATGATCAAA CCCAGAATTG TTCTCCTTAT
6301   TTTTGTTTCT GGAAAAGTTG TATTAACAGG TGCTAAAGTC AGAGCAGAAA TTTATGAAGC
6361   ATTTGAAAAC ATCTACCCTA TTCTAAAGGG ATTCAGGAAG ACGACGCGGT CCGGCCACCA
6421   TCATCACCAC CATTGATAAG CTAGCGGCCG CTTTCGAATC TAGAGCCTGC AGTCTCGACA
6481   AGCTTGTCGA GAAGTACTAG AGGATCATAA TCAGCCATAC CACATTTGTA GAGGTTTTAC
6541   TTGCTTTAAA AAACCTCCCA CACCTCCCCC TGAACCTGAA ACATAAAATG AATGCAATTG
6601   TTGTTGTTAA CTTGTTTATT GCAGCTTATA ATGGTTACAA ATAAAGCAAT AGCATCACAA
6661   ATTTCACAAA TAAAGCATTT TTTTCACTGC ATTCTAGTTG TGGTTTGTCC AAACTCATCA
6721   ATGTATCTTA TCATGTCTGG ATCTGATCAC TGCTTGAGCC TAGGAGATCC GAACCAGATA
6781   AGTGAAATCT AGTTCCAAAC TATTTTGTCA TTTTTAATTT TCGTATTAGC TTACGACGCT
6841   ACACCCAGTT CCCATCTATT TTGTCACTCT TCCCTAAATA ATCCTTAAAA ACTCCATTTC
6901   CACCCCTCCC AGTTCCCAAC GCCAACTCCA TGTGACAAAC CGTCATCTTC GGCTACTTT
```

Fig. 10

```
SEQ  pUCDMCSTAF1TBPcTAF2: 12950 bp;
Composition  3820 A; 2716 C; 3059 G; 3355 T; 0 OTHER
Percentage:  29.5%  A; 21.0%  C; 23.6%  G; 25.9%  T; 0.0%OTHER
Molecular Weight (kDa): ssDNA: 4006.92 dsDNA: 7982.98
KEYWORD      CIRCULAR

ORIGIN
1       AATTCTGTCA GCCGTTAAGT GTTCCTGTGT CACTGAAAAT TGCTTTGAGA GGCTCTAAGG
61      GCTTCTCAGT GCGTTACATC CCTGGCTTGT TGTCCACAAC CGTTAAACCT TAAAAGCTTT
121     AAAAGCCTTA TATATTCTTT TTTTTCTTAT AAAACTTAAA ACCTTAGAGG CTATTTAAGT
181     TGCTGATTTA TATTAATTTT ATTGTTCAAA CATGAGAGCT TAGTACGTGA AACATGAGAG
241     CTTAGTACGT TAGCCATGAG AGCTTAGTAC GTTAGCCATG AGGGTTTAGT TCGTTAAACA
301     TGAGAGCTTA GTACGTTAAA CATGAGAGCT TAGTACGTGA AACATGAGAG CTTAGTACGT
361     ACTATCAACA GGTTGAACTG CTGATCAACA GATCCTCTAC GCGGCCGCGG TACCATAACT
421     TCGTATAGCA TACATTATAC GAAGTTATCT GGAGTACCCG TAGTGGCTAT GGCAGGGCTT
481     GCCGCCCCGA CGTTGGCTGC GAGCCCTGGG CCTTCACCCG AACTTGGGGG TTGGGGTGGG
541     GAAAAGGAAG AAACGCGGGC GTATTGGTCC CAATGGGGTC TCGGTGGGGT ATCGACAGAG
601     TGCCAGCCCT GGGACCGAAC CCCGCGTTTA TGAACAAACG ACCCAACACC CGTGCGTTTT
661     ATTCTGTCTT TTTATTGCCG TCATAGCGCG GGTTCCTTCC GGTATTGTCT CCTTCCGTGT
721     TTCAGTTAGC CTCCCCCATC TCCCGGTACC GCATGCTATG CATCAGCTGC TAGCACCATG
781     GCTCGAGATC CCGGGTGATC AAGTCTTCGT CGAGTGATTG TAAATAAAAT GTAATTTACA
841     GTATAGTATT TTAATTAATA TACAAATGAT TTGATAATAA TTCTTATTTA ACTATAATAT
901     ATTGTGTTGG GTTGAATTAA AGGTCCGTAT ACTAGTATCG ATTCGCGACC TACTCCGGAA
961     TATTAATAGA TCATGGAGAT AATTAAAATG ATAACCATCT CGCAAATAAA TAAGTATTTT
1021    ACTGTTTTCG TAACAGTTTT GTAATAAAAA AACCTATAAA TATTCCGGAT TATTCATACC
1081    GTCCCACCAT CGGGCGCGGA TCCTCGAGAT GGGTAACCAT GACAAGCGAC GATGGAAAAA
1141    GAATTTCATA GCCGTCTCAG CAGCCAACCG CTTTAAGAAA ATCTCATCCT CCGGGGCAGC
1201    TAGCTGGAGC CACCCGCAGT TCGAAAAAGG CGCCGACGAC GACGACGACA AGGGCTCCCA
1261    TATGGGACCC GGCTGCGATT TGCTGCTGCG GACAGCAGCT ACCATCACTG CTGCCGCCAT
1321    CATGTCAGAC ACGGACAGCG ACGAAGATTC CGCTGGAGGC GGCCCATTTT CTTTAGCGGG
1381    TTTCCTTTTC GGCAACATCA ATGGAGCCGG GCAGCTGGAG GGGGAAAGCG TCTTGGATGA
1441    TGAATGTAAG AAGCACTTGG CAGGCTTGGG GGCTTTGGGG CTGGGCAGCC TGATCACTGA
1501    ACTCACGGCA AATGAAGAAT TGACCGGGAC TGACGGTGCC TTGGTAAATG ATGAAGGGTG
1561    GGTTAGGAGT ACAGAAGATG CTGTGGACTA TTCAGACATC AATGAGGTGG CAGAAGATGA
1621    AAGCCGAAGA TACCAGCAGA CGATGGGGAG CTTGCAGCCC CTTTGCCACT CAGATTATGA
1681    TGAAGATGAC TATGATGCTG ATTGTGAAGA CATTGATTGC AAGTTGATGC CTCCTCCACC
1741    TCCACCCCCG GGACCAATGA AGAAGGATAA GGACCAGGAT TCTATTACTG GTGAGAAAGT
1801    GGACTTCAGT AGTTCCTCTG ACTCAGAATC TGAGATGGGA CCTCAGGAAG CAACACAGGC
1861    AGAATCTGAA GATGGAAAGC TGACCCTTCC ATTGGCTGGG ATTATGCAGC ATGATGCCAC
1921    CAAGCTGTTG CCAAGTGTCA CAGAACTTTT TCCAGAATTT CGACCTGGAA AGGTGTTACG
1981    TTTTCTACGT CTTTTTGGAC CAGGGAAGAA TGTCCCATCT GTTTGGCGGA GTGCTCGGAG
2041    AAAGAGGAAG AAGAAGCACC GTGAGCTGAT ACAGGAAGAG CAGATCCAGG AGGTGGAGTG
2101    CTCAGTAGAA TCAGAAGTCA GCCAGAAGTC TTTGTGGAAC TACGACTACG CTCCACCACC
2161    ACCTCCAGAG CAGTGTCTCT CTGATGATGA AATCACGATG ATGGCTCCTG TGGAGTCCAA
2221    ATTTTCCCAA TCAACTGGAG ATATAGATAA AGTGACAGAT ACCAAACCAA GAGTGGCTGA
2281    GTGGCGTTAT GGGCCTGCCC GACTGTGGTA TGATATGCTG GGTGTCCCTG AAGATGGCAG
2341    TGGGTTTGAC TATGGCTTCA AACTGAGAAA GACAGAACAT GAACCTGTGA TAAAATCTAG
2401    AATGATAGAG GAATTTAGGA AACTTGAGGA AAACAATGGC ACTGATCTTC TGGCTGATGA
2461    AAACTTCCTG ATGGTGACAC AGCTGCATTG GGAGGATGAT ATCATCTGGG ATGGGGAGGA
2521    TGTCAAACAC AAAGGGACAA AACCTCAGCG TGCAAGCCTG GCAGGCTGGC TTCCTTCTAG
2581    CATGACTAGG AATGCGATGG CTTACAATGT TCAGCAAGGT TTTGCAGCCA CTCTTGATGA
2641    TGACAAACCT TGGTACTCCA TTTTTCCCAT TGACAATGAG GATCTGGTAT ATGGACGCTG
2701    GGAGGACAAT ATCATTTGGG ATGCTCAGGC CATGCCCCGG CTGTTGGAAC CTCCTGTTTT
2761    GACACTTGAT CCCAATGATG AGAACCTCAT TTTGGAAATT CCTGATGAGA AGGAAGAGGC
2821    CACCTCTAAC TCCCCCTCCA AGGAGAGTAA GAAGGAATCA TCTCTGAAGA AGAGTCGAAT
```

Fig. 10 (cont'd)

```
2881  TCTCTTAGGG AAAACAGGAG TCATCAAGGA GGAACCACAG CAGAACATGT CTCAGCCAGA
2941  AGTGAAAGAT CCATGGAATC TCTCCAATGA TGAGTATTAT TATCCCAAGC AACAGGGTCT
3001  TCGAGGCACC TTTGGAGGGA ATATTATCCA GCATTCAATT CCTGCTGTGG AATTACGGCA
3061  GCCCTTCTTT CCCACCCACA TGGGGCCCAT CAAACTCCGG CAGTTCCATC GCCCCACCTCT
3121  GAAAAAGTAC TCATTTGGTG CACTTTCTCA GCCAGGTCCC CACTCAGTCC AACCTTTGCT
3181  AAAGCACATC AAAAAAAAGG CCAAGATGAG AGAACAAGAG AGGCAAGCTT CAGGTGGTGG
3241  AGAGATGTTT TTTATGCGCA CACCTCAGGA CCTCACAGGC AAAGATGGTG ATCTTATTCT
3301  TGCAGAATAT AGTGAGGAAA ATGGACCCTT AATGATGCAG GTTGGCATGG CAACCAAGAT
3361  AAAGAACTAT TATAAACGGA AACCTGGAAA AGATCCTGGA GCACCAGATT GTAAATATGG
3421  GGAAACTGTT TACTGCCATA CATCTCCTTT CCTGGGTTCT CTCCATCCTG GCCAATTGCT
3481  GCAAGCATTT GAGAACAACC TTTTTCGTGC TCCAATTTAT CTTCATAAGA TGCCAGAAAC
3541  TGATTTCTTG ATCATTCGGA CAAGACAGGG TTACTATATT CGGGAATTAG TGGATATTTT
3601  TGTGGTTGGC CAGCAGTGTC CCTTGTTTGA AGTTCCTGGG CCTAACTCCA AAAGGGCCAA
3661  TACGCATATT CGAGACTTTC TACAGGTTTT TATTTACCGC CTTTTCTGGA AAAGTAAAGA
3721  TCGGCCACGG AGGATACGAA TGGAAGATAT AAAAAAAGCC TTTCCTTCCC ATTCAGAAAG
3781  CAGCATCCGG AAGAGGCTAA AGCTCTGCGC TGACTTCAAA CGCACAGGGA TGGACTCAAA
3841  CTGGTGGGTG CTTAAGTCTG ATTTTCGTTT ACCAACGGAA GAAGAGATCA GAGCTATGGT
3901  GTCACCAGAG CAGTGCTGTG CTTATTATAG CATGATAGCT GCAGAGCAAC GACTGAAGGA
3961  TGCTGGCTAT GGTGAGAAAT CCTTTTTTGC TCCAGAAGAA GAAAATGAGG AAGATTTCCA
4021  GATGAAGATT GATGATGAAG TTCGCACTGC CCCTTGGAAC ACCACAAGGG CCTTCATTGC
4081  TGCCATGAAG GGCAAGTGTC TGCTAGAGGT GACTGGGGTG GCAGATCCCA CGGGGTGTGG
4141  TGAAGGATTC TCCTATGTGA AGATTCCAAA CAAACCAACA CAGCAGAAGG ATGATAAAGA
4201  ACCGCAGCCA GTGAAGAAGA CAGTGACAGG AACAGATGCA GACCTTCGTC GCCTTTCCCT
4261  GAAAAATGCC AAGCAACTTC TACGTAAATT TGGTGTGCCT GAGGAAGAGA TTAAAAAGTT
4321  GTCCCGCTGG GAAGTGATTG ATGTGGTGCG CACAATGTCA ACAGAACAGG CTCGTTCTGG
4381  AGAGGGGCCC ATGAGTAAAT TTGCCCGTGG ATCAAGGTTT TCTGTGGCTG AGCATCAAGA
4441  GCGTTACAAA GAGGAATGTC AGCGCATCTT TGACCTACAG AACAAGGTTC TGTCATCAAC
4501  TGAAGTCTTA TCAACTGACA CAGACAGCAG CTCAGCTGAA GATAGTGACT TTGAAGAAAT
4561  GGGAAAGAAC ATTGAGAACA TGTTGCAGAA CAAGAAAACC AGCTCTCAGC TTTCACGTGA
4621  ACGGGAGGAA CAGGAGCGGA AGGAACTACA GCGAATGCTA CTGGCAGCAG GCTCAGCAGC
4681  ATCCGGAAAC AATCACAGAG ATGATGACAC AGCTTCCGTG ACTAGCCTTA ACTCTTCTGC
4741  CACTGGACGC TGTCTCAAGA TTTATCGCAC GTTTCGAGAT GAAGAGGGGA AAGAGTATGT
4801  TCGCTGTGAG ACAGTCCGAA AACCAGCTGT CATTGATGCC TATGTGCGCA TACGGACTAC
4861  AAAAGATGAG GAATTCATTC GAAAATTTGC CCTTTTTGAT GAACAACATC GGGAAGAGAT
4921  GCGAAAAGAA CGGCGGAGGA TTCAAGAGCA ACTGAGGCGG CTTAAGAGGA ACCAGGAAAA
4981  GGAGAAGCTT AAGGGTCCTC CTGAGAAGAA GCCCAAGAAA ATGAAGGAGC GTCCTGACCT
5041  AAAACTGAAA TGTGGGGCAT GTGGTGCCAT TGGACACATG AGGACTAACA AATTCTGCCC
5101  CCTCTATTAT CAAACAAATG CGCCACCTTC CAACCCTGTT GCCATGACAG AAGAACAGGA
5161  GGAGGAGTTG GAAAAGACAG TCATTCATAA TGATAATGAA GAACTTATCA AGGTTGAAGG
5221  GACCAAAATT GTCTTGGGGA AACAGCTAAT TGAGAGTGCG GATGAGGTTC GCAGAAAATC
5281  TCTGGTTCTC AAGTTTCCTA AACAGCAGCT TCCTCCAAAG AAGAAACGGC GAGTTGGAAC
5341  CACTGTTCAC TGTGACTATT TGAATAGACC TCATAAGTCC ATCCACCGGC GCCGCACAGA
5401  CCCTATGGTG ACGCTGTCGT CCATCTTGGA GTCTATCATC AATGACATGA GAGATCTTCC
5461  AAATACATAC CCTTTCCACA CTCCAGTCAA TGCAAAGGTT GTAAAGGACT ACTACAAAAT
5521  CATCACTCGG CCAATGGACC TACAAACACT CCGCGAAAAC GTGCGTAAAC GCCTCTACCC
5581  ATCTCGGGAA GAGTTCAGAG AGCATCTGGA GCTAATTGTG AAAAATAGTG CAACCTACAA
5641  TGGGCCAAAA CACTCATTGA CTCAGATCTC TCAATCCATG CTGGATCTCT GTGATGAAAA
5701  ACTCAAAGAG AAAGAAGACA AATTAGCTCG CTTAGAGAAA GCTATCAACC CCTTGCTGGA
5761  TGATGATGAC CAAGTGGCGT TTTCTTTCAT TCTGGACAAC ATTGTCACCC AGAAAATGAT
5821  GGCAGTTCCA GATTCTTGGC CATTTCATCA CCCAGTTAAT AAGAAATTTG TTCCAGATTA
5881  TTACAAAGTG ATTGTCAATC CAATGGATTT AGAGACCATA CGTAAGAACA TCTCCAAGCA
5941  CAAGTATCAG AGTCGGGAGA GCTTTCTGGA TGATGTAAAC CTTATTCTGG CCAACAGTGT
6001  TAAGTATAAT GGACCTGAGA GTCAGTATAC TAAGACTGCC CAGGAGATTG TGAACGTCTG
6061  TTACCAGACA TTGACTGAGT ATGATGAACA TTTGACTCAA CTTGAGAAGG ATATTTGTAC
```

Fig. 10 (cont'd)

```
6121  TGCTAAAGAA GCAGCTTTGG AGGAAGCAGA ATTAGAAAGC CTGGACCCAA TGACCCCAGG
6181  GCCCTACACG CCTCAGCCTC CTGATTTGTA TGATACCAAC ACATCCCTCA GTATGTCTCG
6241  AGATGCCTCT GTATTTCAAG ATGAGAGCAA TATGTCTGTC TTGGATATTC CCAGTGCCAC
6301  TCCAGAAAAG CAGGTAACAC AGGAAGGTGA AGATGGAGAT GGTGATCTTG CAGATGAAGA
6361  GGAAGGAACT GTACAACAGC CTCAAGCCAG TGTCCTGTAT GAGGATTTGC TTATGTCTGA
6421  AGGAGAAGAT GATGAGGAAG ATGCTGGGAG TGATGAAGAA GGAGACAATC CTTTCTCTGC
6481  TATCCAGCTG AGTGAAAGTG GAAGTGACTC TGATGTGGGA TCTGGTGGAA TAAGACCCAA
6541  ACAACCCCGC ATGCTTCAGG AGAACACAAG GATGGACATG GAAAATGAAG AAAGCATGAT
6601  GTCCTATGAG GGAGACGGTG GGGAGGCTTC CCATGGTTTG GAGGATAGCA ACATCAGTTA
6661  TGGGAGCTAT GAGGAGCCTG ATCCCAAGTC GAACACCCAA GACACAAGCT TCAGCAGCAT
6721  CGGTGGGTAT GAGGTATCAG AGGAGGAAGA AGATGAGGAG GAGGAAGAGC AGCGCTCTGG
6781  GCCGAGCGTA CTAAGCCAGG TCCACCTGTC AGAGGACGAG GAGGACAGTG AGGATTTCCA
6841  CTCCATTGCT GGGGACAGTG ACTTGGACTC TGATGAACGG TCCGGAGGTA ACGGATCCGA
6901  AAACCTGTAT TTTCAGGGTT CTGGGATTGT ACCGCAGCTG CAAAATATTG TATCCACAGT
6961  GAATCTTGGT TGTAAACTTG ACCTAAAGAC CATTGCACTT CGTGCCCGAA ACGCCGAATA
7021  TAATCCCAAG CGGTTTGCTG CGGTAATCAT GAGGATAAGA GAGCCACGAA CCACGGCACT
7081  GATTTTCAGT TCTGGGAAAA TGGTGTGCAC AGGAGCCAAG AGTGAAGAAC AGTCCAGACT
7141  GGCAGCAAGA AAATATGCTA GAGTTGTACA GAAGTTGGGT TTTCCAGCTA AGTTCTTGGA
7201  CTTCAAGATT CAGAACATGG TGGGGAGCTG TGATGTGAAG TTTCCTATAA GGTTAGAAGG
7261  CCTTGTGCTC ACCCACCAAC AATTTAGTAG TTATGAGCCA GAGTTATTTC CTGGTTTAAT
7321  CTACAGAATG ATCAAACCCA GAATTGTTCT CCTTATTTTT GTTTCTGGAA AAGTTGTATT
7381  AACAGGTGCT AAAGTCAGAG CAGAAATTTA TGAAGCATTT GAAAACATCT ACCCTATTCT
7441  AAAGGGATTC AGGAAGACGA CGCGGTCCGG AGGTAACGGA TCCGAAAACC TGTATTTTCA
7501  GGGTGACTAC AAAGACGATG ACGATAAAAA CAGGAAGAAA GGAGACAAGG GCTTTGAAAG
7561  CCCAAGGCCA TATAAATTAA CCCATCAGGT CGTCTGCATC AACAACATAA ATTTCCAGAG
7621  AAAATCTGTT GTGGGATTTG TGGAACTGAC TATATTTCCC ACAGTTGCAA ACTTGAATAG
7681  AATCAAGTTG AACAGCAAAC AGTGTAGAAT ATACCGAGTA AGGATCAATG ATTTAGAGGC
7741  TGCTTTTATT TATAATGACC CAACCTTGGA AGTTTGTCAC AGTGAATCAA AACAGAGAAA
7801  CCTCAATTAT TTTTCCAATG CTTATGCAGC TGCAGTTAGT GCTGTGGACC CTGATGCAGG
7861  AAATGGAGAA CTTTGCATTA AGGTTCCATC AGAGCTATGG AAACACGTTG ATGAGTTAAA
7921  GGTCCTGAAG ATACACATCA ATTTTTCTTT GGATCAGCCC AAAGGAGGTC TTCATTTTGT
7981  GGTACCCAGT GTAGAGGGAA GTATGGCAGA GAGAGGTGCT CATGTTTTCT CTTGTGGGTA
8041  TCAAAATTCT ACAAGATTTT GGTTCCCTTG TGTTGATTCA TACTCTGAAT TGTGTACATG
8101  GAAATTAGAA TTTACAGTAG ATGCTGCAAT GGTTGCTGTT TCTAATGGCG ATTTGGTGGA
8161  GACAGTGTAT ACTCATGATA TGAGGAAGAA AACTTTCCAT TATATGCTTA CCATTCCTAC
8221  AGCAGCGTCA AATATCTCCT TGGCCATTGG ACCATTTGAA ATACTGGTAG ATCCATACAT
8281  GCATGAGGTT ACTCATTTTT GTTTGCCCCA ACTTCTTCCA TTGCTGAAAC ATACCACATC
8341  ATACCTTCAT GAAGTCTTTG AATTTTATGA AGAAATTCTT ACATGTCGTT ACCCATACTC
8401  CTGTTTTAAG ACTGTCTTCA TTGATGAGGC TTATGTTGAA GTGGCTGCTT ATGCTTCCAT
8461  GAGCATTTTT AGCACAAATC TTTTACACAG TGCCATGATT ATAGATGAGA CACCTTTGAC
8521  TAGAAGGTGT TTAGCCCAAT CCTTGGCCCA GCAGTTTTTT GGTTGTTTCA TATCTAGAAT
8581  GTCTTGGTCT GATGAATGGG TGCTGAAGGG AATTTCAGGC TATATCTATG GACTTTGGAT
8641  GAAAAAAACT TTTGGTGTTA ATGAGTACCG CCATTGGATT AAAGAGGAGC TAGACAAAAT
8701  AGTGGCATAT GAACTAAAAA CTGGTGGGGT TTTACTACAT CCCATATTTG GTGGAGGAAA
8761  AGAGAAGGAT AATCCGGCTT CCCATCTACA CTTTTCAATA AAGCATCCAC ATACACTGTC
8821  CTGGGAATAC TACACTATGT TTCAGTGTAA AGCCCACCTT GTGATGAGAT TGATTGAAAA
8881  TAGGATCAGT ATGGAATTTA TGCTACAAGT TTTCAATAAA CTGCTAAGTC TGGCTAGTAC
8941  TGCTTCATCT CAGAAGTTCC AGTCACATAT GTGGAGTCAG ATGTTGGTTT CCACATCTGG
9001  GTTTTTGAAA TCCATTTCAA ATGTCTCTGG CAAAGATATT CAGCCGTTAA TAAAGCAGTG
9061  GGTAGATCAG AGTGGAGTGG TAAAATTTTA TGGAAGTTTT GCATTTAATA GAAAACGAAA
9121  TGTCTTGGAA CTGGAAATAA AACAGGACTA TACATCTCCT GGAACTCAGA AATACGTGGG
9181  ACCACTTAAA GTGACAGTGC AGGAGTTAGA TGGATCCTTC AATCATACAC TGCAAATTGA
9241  AGAAAACAGC CTTAAACATG ATATACCCTG CCATTCCAAA AGTAGAAGGA ATAAAAAGAA
9301  AAAAATCCCA CTGATGAATG GAGAAGAAGT TGACATGGAT CTTTCTGCAA TGGATGCTGA
9361  TTCCCCTTTG CTGTGGATAA GGATAGACCC AGATATGTCA GTATTGAGGA AGGTAGAATT
```

Fig. 10 (cont'd)

```
9421  TGAGCAAGCT GATTTTATGT GGCAGTATCA GCTCCGCTAT GAGAGAGATG TTGTTGCACA
9481  GCAGGAATCC ATTTTGGCTT TGGAAAAATT CCCTACTCCA GCATCTCGGC TTGCACTCAC
9541  TGATATATTA GAACAAGAGC AGTGTTTCTA CAGAGTAAGA ATGTCAGCTT GCTTCTGTCT
9601  TGCAAAGATT GCAAATTCCA TGGTGAGCAC ATGGACAGGA CCACCAGCCA TGAAGTCACT
9661  CTTCACTAGG ATGTTTTGTT GTAAAAGTTG TCCAAACATT GTGAAAACAA ACAACTTTAT
9721  GAGCTTTCAA AGTTATTTTC TACAGAAGAC TATGCCAGTT GCAATGGCTT TATTAAGAGA
9781  TGTTCATAAT CTTTGTCCTA AAGAAGTCTT AACGTTTATT TTAGACTTAA TCAAGTACAA
9841  TGACAACAGG AAAAATAAGT TTTCAGATAA CTATTATCGT GCAGAAATGA TTGATGCCCT
9901  GGCCAACTCT GTTACACCTG CAGTCAGTGT GAATAATGAA GTTAGAACTT TGGATAACTT
9961  AAATCCTGAT GTGCGACTCA TTCTTGAAGA AATCACCAGA TTTTTGAATA TGGAAAAACT
10021 TCTTCCGAGT TACAGGCATA CCATCACTGT CAGTTGTTTG AGAGCCATAC GGGTACTTCA
10081 GAAGAACGGA CATGTGCCAA GTGATCCAGC TCTTTTTAAA TCTTATGCTG AATATGGCCA
10141 CTTTGTGGAC ATTAGGATAG CAGCTTTGGA AGCAGTTGTT GATTATACTA AAGTGGACAG
10201 AAGTTATGAA GAACTGCAAT GGCTACTTAA TATGATTCAG AATGACCCTG TACCCTATGT
10261 AAGGCATAAG ATTCTCAACA TGTTGACTAA GAACCCACCA TTTACTAAGA ACATGGAGTC
10321 TCCCTTATGC AATGAAGCCC TGGTAGATCA ACTTTGGAAA CTTATGAATT CTGGTACTTC
10381 ACATGACTGG AGGTTACGGT GTGGTGCTGT GGACTTGTAC TTCACACTTT TTGGCCTCAG
10441 TAGACCTTCC TGTTTACCCT TGCCAGAGCT TGGGTTGGTT CTTAATCTAA AGGAGAAAAA
10501 AGCTGTCTTG AATCCTACCA TAATTCCAGA GTCAGTAGCA GGCAACCAAG AAGCTGCAAA
10561 TAATCCAAGC AGTCACCCAC AGCTAGTTGG ATTTCAGAAC CCTTTTTCCA GTTCTCAAGA
10621 TGAGGAGGAG ATTGATATGG ATACTGTTCA TGATAGCCAG GCCTTCATTT CCCATCATTT
10681 AAACATGCTT GAAAGGCCGT CAACTCCAGG GCTCTCGAAG TATCGGCCAG CTAGCTCCCG
10741 ATCTGCTTTA ATACCCCAGC ACTCAGCAGG CTGCGACAGC ACACCCACCA CAAAACCCCA
10801 GTGGAGTTTG GAACTTGCAC GGAAGGGAAC AGGTAAAGAA CAAGCACCTT TGGAGATGAG
10861 TATGCATCCG GCGGCAAGCG CTCCACTCTC AGTCTTTACT AAGGAATCTA CAGCCTCCAA
10921 ACACAGTGAC CACCATCACC ACCATCACCA TGAGCACAAG AAAAAGAAGA AGAAGCATAA
10981 ACATAAGCAC AAACACAAGC ATAAGCATGA CAGTAAAGAA AAGGACAAGG AGCCTTTCAC
11041 TTTCTCCAGC CCTGCCAGTG GCAGGTCTAT TCGTTCTCCT TCCCTTTCAG ACCGGTCCGG
11101 CCACCATCAT CACCACCATT GATAAGCTAG CGGCCGCTTT CGAATCTAGA GCCTGCAGTC
11161 TCGACAAGCT TGTCGAGAAG TACTAGAGGA TCATAATCAG CCATACCACA TTTGTAGAGG
11221 TTTTACTTGC TTTAAAAAAC CTCCCACACC TCCCCCTGAA CCTGAAACAT AAAATGAATG
11281 CAATTGTTGT TGTTAACTTG TTTATTGCAG CTTATAATGG TTACAAATAA AGCAATAGCA
11341 TCACAAATTT CACAAATAAA GCATTTTTTT CACTGCATTC TAGTTGTGGT TTGTCCAAAC
11401 TCATCAATGT ATCTTATCAT GTCTGGATCT GATCACTGCT TGAGCCTAGA AGATCCGGCT
11461 GCTAACAAAG CCCGAAAGGA AGCTGAGTTG GCTGCTGCCA CCGCTGAGCA ATAACTAGCA
11521 TAACCCCTTG GGGCCTCTAA ACGGGTCTTG AGGGGTTTTT TGCTGAAAGG AGGAACTATA
11581 TCCGGATCTG AACAGGAGGG ACAGCTGATA GAAACAGAAG CCACTGGAGC ACCTCAAAAA
11641 CACCATCATA CACTAAATCA GTAAGTTGGC AGCATCACCC GACGCACTTT GCGCCGAATA
11701 AATACCTGTG ACGGAAGATC ACTTCGCAGA ATAAATAAAT CCTGGTGTCC CTGTTGATAC
11761 CGGGAAGCCC TGGGCCAACT TTTGGCGAAA ATGAGACGTT GATCGGCACG TAAGAGGTTC
11821 CAACTTTCAC CATAATGAAA TAAGATCACT ACCGGGCGTA TTTTTTGAGT TATCGAGATT
11881 TTCAGGAGCT AAGGAAGCTA AAATGGAGAA AAAAATCACT GGATATACCA CCGTTGATAT
11941 ATCCCAATGG CATCGTAAAG AACATTTTGA GGCATTTCAG TCAGTTGCTC AATGTACCTA
12001 TAACCAGACC GTTCAGCTGG ATATTACGGC CTTTTTAAAG ACCGTAAAGA AAAATAAGCA
12061 CAAGTTTTAT CCGGCCTTTA TTCACATTCT TGCCCGCCTG ATGAATGCTC ATCCGGAATT
12121 CCGTATGGCA ATGAAAGACG GTGAGCTGGT GATATGGGAT AGTGTTCACC CTTGTTACAC
12181 CGTTTTCCAT GAGCAAACTG AAACGTTTTC ATCGCTCTGG AGTGAATACC ACGACGATTT
12241 CCGGCAGTTT CTACACATAT ATTCGCAAGA TGTGGCGTGT TACGGTGAAA ACCTGGCCTA
12301 TTTCCCTAAA GGGTTTATTG AGAATATGTT TTTCGTCTCA GCCAATCCCT GGGTGAGTTT
12361 CACCAGTTTT GATTTAAACG TGGCCAATAT GGACAACTTC TTCGCCCCCG TTTTCACCAT
12421 GGGCAAATAT TATACGCAAG GCGACAAGGT GCTGATGCCG CTGGCGATTC AGGTTCATCA
12481 TGCCGTCTGT GATGGCTTCC ATGTCGGCAG AATGCTTAAT GAATTACAAC AGTACTGCGA
12541 TGAGTGGCAG GGCGGGGCGT AATTTTTTTA AGGCAGTTAT TGGTGCCCTT AAACGCCTGG
12601 TGCTACGCCT GAATAAGTGA TAATAAGCGG ATGAATGGCA GAAATTCGAA AGCAAATTCG
12661 ACCCGGTCGT CGGTTCAGGG CAGGGTCGTT AAATAGCCGC TTATGTCTAT TGCTGGTTTA
```

```
12721  CCGGTTTATT GACTACCGGA AGCAGTGTGA CCGTGTGCTT CTCAAATGCC TGAGGCCAGT
12781  TTGCTCAGGC TCTCCCCGTG GAGGTAATAA TTGACGATAT GATCATTTAT TCTGCCTCCC
12841  AGAGCCTGAC ATTCATCCGG GGTCAGCACC GTTTCTGCGG ACTGGCTTTC TACGTGTTCC
12901  GCTTCCTTTA GCAGCCCTTG CGCCCTGAGT GCTTGCGGCA GCGTGAAGCT
```

pFBDO[HisTEVTAF6TAF9]his

Fig. 12

```
SEQ  pFBDO[HisTEV8032]his: 8735 bp;
Composition  2196 A; 2272 C; 2120 G; 2147 T; 0 OTHER
Percentage:  25.1% A; 26.0% C; 24.3% G; 24.6% T; 0.0%OTHER
Molecular Weight (kDa): ssDNA: 2694.12 dsDNA: 5385.15
KEYWORD     CIRCULAR

ORIGIN
1      TTCTCTGTCA CAGAATGAAA ATTTTTCTGT CATCTCTTCG TTATTAATGT TTGTAATTGA
61     CTGAATATCA ACGCTTATTT GCAGCCTGAA TGGCGAATGG GACGCGCCCT GTAGCGGCGC
121    ATTAAGCGCG GCGGGTGTGG TGGTTACGCG CAGCGTGACC GCTACACTTG CCAGCGCCCT
181    AGCGCCCGCT CCTTTCGCTT TCTTCCCTTC CTTTCTCGCC ACGTTCGCCG GCTTTCCCCG
241    TCAAGCTCTA AATCGGGGGC TCCCTTTAGG GTTCCGATTT AGTGCTTTAC GGCACCTCGA
301    CCCCAAAAAA CTTGATTAGG GTGATGGTTC ACGTAGTGGG CCATCGCCCT GATAGACGGT
361    TTTTCGCCCT TTGACGTTGG AGTCCACGTT CTTTAATAGT GGACTCTTGT TCCAAACTGG
421    AACAACACTC AACCCTATCT CGGTCTATTC TTTTGATTTA TAAGGGATTT TGCCGATTTC
481    GGCCTATTGG TTAAAAAATG AGCTGATTTA ACAAAAATTT AACGCGAATT TTAACAAAAT
541    ATTAACGTTT ACAATTTCAG GTGGCACTTT TCGGGGAAAT GTGCGCGGAA CCCCTATTTG
601    TTTATTTTTC TAAATACATT CAAATATGTA TCCGCTCATG AGACAATAAC CCTGATAAAT
661    GCTTCAATAA TATTGAAAAA GGAAGAGTAT GAGTATTCAA CATTTCCGTG TCGCCCTTAT
721    TCCCTTTTTT GCGGCATTTT GCCTTCCTGT TTTTGCTCAC CCAGAAACGC TGGTGAAAGT
781    AAAAGATGCT GAAGATCAGT TGGGTGCACG AGTGGGTTAC ATCGAACTGG ATCTCAACAG
841    CGGTAAGATC CTTGAGAGTT TTCGCCCCGA AGAACGTTTT CCAATGATGA GCACTTTTAA
901    AGTTCTGCTA TGTGGCGCGG TATTATCCCG TATTGACGCC GGGCAAGAGC AACTCGGTCG
961    CCGCATACAC TATTCTCAGA ATGACTTGGT TGAGTACTCA CCAGTCACAG AAAAGCATCT
1021   TACGGATGGC ATGACAGTAA GAGAATTATG CAGTGCTGCC ATAACCATGA GTGATAACAC
1081   TGCGGCCAAC TTACTTCTGA CAACGATCGG AGGACCGAAG GAGCTAACCG CTTTTTTGCA
1141   CAACATGGGG GATCATGTAA CTCGCCTTGA TCGTTGGGAA CCGGAGCTGA ATGAAGCCAT
1201   ACCAAACGAC GAGCGTGACA CCACGATGCC TGTAGCAATG GCAACAACGT TGCGCAAACT
1261   ATTAACTGGC GAACTACTTA CTCTAGCTTC CCGGCAACAA TTAATAGACT GGATGGAGGC
1321   GGATAAAGTT GCAGGACCAC TTCTGCGCTC GGCCCTTCCG GCTGGCTGGT TTATTGCTGA
1381   TAAATCTGGA GCCGGTGAGC GTGGGTCTCG CGGTATCATT GCAGCACTGG GGCCAGATGG
1441   TAAGCCCTCC CGTATCGTAG TTATCTACAC GACGGGGAGT CAGGCAACTA TGGATGAACG
1501   AAATAGACAG ATCGCTGAGA TAGGTGCCTC ACTGATTAAG CATTGGTAAC TGTCAGACCA
1561   AGTTTACTCA TATATACTTT AGATTGATTT AAAACTTCAT TTTTAATTTA AAAGGATCTA
1621   GGTGAAGATC CTTTTTGATA ATCTCATGAC CAAAATCCCT TAACGTGAGT TTTCGTTCCA
1681   CGTAATCTGC TGCTTGCAAA CAAAAAAACC ACCGCTACCA GCGGTGGTTT GTTTGCCGGA
1741   TCAAGAGCTA CCAACTCTTT TTCCGAAGGT AACTGGCTTC AGCAGAGCGC AGATACCAAA
1801   TACTGTCCTT CTAGTGTAGC CGTAGTTAGG CCACCACTTC AAGAACTCTG TAGCACCGCC
1861   TACATACCTC GCTCTGCTAA TCCTGTTACC AGTGGCTGCT GCCAGTGGCG ATAAGTCGTG
1921   TCTTACCGGG TTGGACTCAA GACGATAGTT ACCGGATAAG GCGCAGCGGT CGGGCTGAAC
1981   GGGGGGTTCG TGCACACAGC CCAGCTTGGA GCGAACGACC TACACCGAAC TGAGATACCT
2041   ACAGCGTGAG CATTGAGAAA GCGCCACGCT TCCCGAAGGG AGAAAGGCGG ACAGGTATCC
2101   GGTAAGCGGC AGGGTCGGAA CAGGAGAGCG CACGAGGGAG CTTCCAGGGG GAAACGCCTG
2161   GTATCTTTAT AGTCCTGTCG GGTTTCGCCA CCTCTGACTT GAGCGTCGAT TTTTGTGATG
2221   CTCGTCAGGG GGGCGGAGCC TATGGAAAAA CGCCAGCAAC GCGGCCTTTT TACGGTTCCT
2281   GGCCTTTTGC TGGCCTTTTG CTCACATGTT CTTTCCTGCG TTATCCCCTG ATTCTGTGGA
2341   TAACCGTATT ACCGCCTTTG AGTGAGCTGA TACCGCTCGC CGCAGCCGAA CGACCGAGCG
2401   CAGCGAGTCA GTGAGCGAGG AAGCGGAAGA GCGCCTGATG CGGTATTTTC TCCTTACGCA
2461   TCTGTGCGGT ATTTCACACC GCAGACCAGC CGCGTAACCT GGCAAAATCG GTTACGGTTG
2521   AGTAATAAAT GGATGCCCTG CGTAAGCGGG TGTGGGCGGA CAATAAAGTC TTAAACTGAA
2581   CAAAATAGAT CTAAACTATG ACAATAAAGT CTTAAACTAG ACAGAATAGT TGTAAACTGA
2641   AATCAGTCCA GTTATGCTGT GAAAAAGCAT ACTGGACTTT TGTTATGGCT AAAGCAAACT
2701   CTTCATTTTC TGAAGTGCAA ATTGCCCGTC GTATTAAAGA GGGGCGTGGC CAAGGGCATG
2761   GTAAAGACTA TATTCGCGGC GTTGTGACAA TTTACCGAAC AACTCCGCGG CCGGGAAGCC
```

Fig. 12 (cont'd)

```
2821 GATCTCGGCT TGAACGAATT GTTAGGTGGC GGTACTTGGG TCGATATCAA AGTGCATCAC
2881 TTCTTCCCGT ATGCCCAACT TTGTATAGAG AGCCACTGCG GGATCGTCAC CGTAATCTGC
2941 TTGCACGTAG ATCACATAAG CACCAAGCGC GTTGGCCTCA TGCTTGAGGA GATTGATGAG
3001 CGCGGTGGCA ATGCCCTGCC TCCGGTGCTC GCCGGAGACT GCGAGATCAT AGATATAGAT
3061 CTCACTACGC GGCTGCTCAA ACCTGGGCAG AACGTAAGCC GCGAGAGCGC CAACAACCGC
3121 TTCTTGGTCG AAGGCAGCAA GCGCGATGAA TGTCTTACTA CGGAGCAAGT TCCCGAGGTA
3181 ATCGGAGTCC GGCTGATGTT GGGAGTAGGT GGCTACGTCT CCGAACTCAC GACCGAAAAG
3241 ATCAAGAGCA GCCCGCATGG ATTTGACTTG GTCAGGGCCG AGCCTACATG TGCGAATGAT
3301 GCCCATACTT GAGCCACCTA ACTTTGTTTT AGGGCGACTG CCCTGCTGCG TAACATCGTT
3361 CTTGCTGCTT GGATGCCCGA GGCATAGACT GTACAAAAAA ACAGTCATAA CAAGCCATGA
3421 AAACCGCCAC TGCGCCGTTA CCACCGCTGC GTTCGGTCAA GGTTCTGGAC CAGTTGCGTG
3481 AGCGCATACG CTACTTGCAT TACAGTTTAC GAACCGAACA GGCTTATGTC AACTGGGTTC
3541 GTGCCTTCAT CCGTTTCCAC GGTGTGCGTC ACCCGGCAAC CTTGGGCAGC AGCGAAGTCG
3601 AGGCATTTCT GTCCTGGCTG GCGAACGAGC GCAAGGTTTC GGTCTCCACG CATCGTCAGG
3661 CATTGGCGGC CTTGCTGTTC TTCTACGGCA AGGTGCTGTG CACGGATCTG CCCTGGCTTC
3721 AGGAGATCGG TAGACCTCGG CCGTCGCGGC GCTTGCCGGT GGTGCTGACC CCGGATGAAG
3781 TGGTTCGCAT CCTCGGTTTT CTGGAAGGCG AGCATCGTTT GTTCGCCCAG GACTCTAGCT
3841 ATAGTTCTAG TGGTTGGCCT ACAGCTTTGT TTAAACAAAG CTGTACCCGT AGTGGCTATG
3901 GCAGGGCTTG CCGCCCCGAC GTTGGCTGCG AGCCCTGGGC CTTCACCCGA ACTTGGGGGT
3961 TGGGGTGGGG AAAAGGAAGA AACGCGGGCG TATTGGTCCC AATGGGGTCT CGGTGGGGTA
4021 TCGACAGAGT GCCAGCCCTG GGACCGAACC CCGCGTTTAT GAACAAACGA CCCAACACCC
4081 GTGCGTTTTA TTCTGTCTTT TTATTGCCGT CATAGCGCGG GTTCCTTCCG GTATTGTCTC
4141 CTTCCGTGTT TCAGTTAGCC TCCCCCATCT CCCGGTACCG CATGCTATGC ATCAGCTGCT
4201 AGCACCATGG CTCGAGATCC CGGGTGATCA AGTCTTCGTC GAGTGATTGT AAATAAAATG
4261 TAATTTACAG TATAGTATTT TAATTAATAT ACAAATGATT TGATAATAAT TCTTATTTAA
4321 CTATAATATA TTGTGTTGGG TTGAATTAAA GGTCCGTATA CTAGTATCGA TTCGCGACCT
4381 ACTCCGGAAT ATTAATAGAT CATGGAGATA ATTAAAATGA TAACCATCTC GCAAATAAAT
4441 AAGTATTTTA CTGTTTTCGT AACAGTTTTG TAATAAAAAA ACCTATAAAT ATTCCGGATT
4501 ATTCATACCG TCCCACCATC GGGCGCGGAT CCTCGAGATG GGTAACCATC ATCATCATCA
4561 TCACGGAGAA AGCTTGTTTA AGGGACCACG TGATTACAAC CCGATATCGA GCACCATTTG
4621 TCATTTGACG AATGAATCTG ATGGGCACAC AACATCGTTG TATGGTATTG GATTTGGTCC
4681 CTTCATCATT ACAAACAAGC ACTTGTTTAG AAGAAATAAT GGAACACTGT TGGTCCAATC
4741 ACTACATGGT GTATTCAAGG TCAAGAACAC CACGACTTTG CAACAACACC TCATTGATGG
4801 GAGGGACATG ATAATTATTC GCATGCCTAA GGATTTCCCA CCATTTCCTC AAAAGCTGAA
4861 ATTTAGAGAG CCACAAAGGG AAGAGCGCAT ATGTCTTGTG ACAACCAACT TCCAAACTAA
4921 GAGCATGTCT AGCATGGTGT CAGACACTAG TTGCACATTC CCTTCATCTG ATGGCATATT
4981 CTGGAAGCAT TGGATTCAAA CCAAGGATGG GCAGTGTGGC AGTCCATTAG TATCAACTAG
5041 AGATGGGTTC ATTGTTGGTA TACACTCAGC ATCGAATTTC ACCAACACAA ACAATTATTT
5101 CACAAGCGTG CCGAAAAACT TCATGGAATT GTTGACAAAT CAGGAGGCGC AGCAGTGGGT
5161 TAGTGGTTGG CGATTAAATG CTGACTCAGT ATTGTGGGGG GGCCATAAAG TTTTCATGAG
5221 CAAACCTGAA GAGCCTTTTC AGCCAGTTAA GGAAGCGACT CAACTCATGA ATGAATTGGT
5281 GTACTCGCAA GGTGGTGGTG AAAACCTGTA CTTCCAGGGT AACCACGCTG AGGAGAAGAA
5341 GCTGAAGCTT AGCAACACTG TGCTGCCCTC GGAGTCCATG AAGGTGGTGG CTGAATCCAT
5401 GGGCATCGCC CAGATTCAGG AGGAGACCTG CCAGCTGCTA ACGGATGAGG TCAGCTACCG
5461 CATCAAAGAG ATCGCACAGG ATGCCTTGAA GTTCATGCAC ATGGGGAAGC GGCAGAAGCT
5521 CACCACCAGT GACATTGACT ACGCCTTGAA GCTAAAGAAT GTCGAGCCAC TCTATGGCTT
5581 CCACGCCCAG GAGTTCATTC CTTTCCGCTT CGCCTCTGGT GGGGGCCGGG AGCTTTACTT
5641 CTATGAGGAG AAGGAGGTTG ATCTGAGCGA CATCATCAAT ACCCCTCTGC CCCGGGTGCC
5701 CCTGGACGTC TGCCTCAAAG CTCATTGGCT GAGCATCGAG GGCTGCCAGC CAGCTATCCC
5761 CGAGAACCCG CCCCCAGCTC CCAAAGAGCA ACAGAAGGCT GAAGCCACAG AACCCCTGAA
5821 GTCAGCCAAG CCAGGCCAGG AGGAAGACGG ACCCCTGAAG GGCAAAGGTC AAGGGGCCAC
5881 CACAGCCGAC GGCAAAGGGA AAGAGAAGAA GGCGCCGCCC TTGCTGGAGG GGGCCCCCTT
5941 GCGACTGAAG CCCCGGAGCA TCCACGAGTT GTCTGTGGAG CAGCAGCTCT ACTACAAGGA
6001 GATCACCGAG GCCTGCGTGG GCTCCTGCGA GGCCAAGAGG GCGGAAGCCC TGCAAAGCAT
6061 TGCCACGGAC CCTGGACTGT ATCAGATGCT GCCACGGTTC AGTACCTTTA TCTCGGAGGG
```

Fig. 12 (cont'd)

```
6121   GGTCCGTGTG AACGTGGTTC AGAACAACCT GGCCCTACTC ATCTACCTGA TGCGTATGGT
6181   GAAAGCGCTG ATGGACAACC CCACGCTCTA TCTAGAAAAA TACGTCCATG AGCTGATTCC
6241   AGCTGTGATG ACCTGCATCG TGAGCAGACA GTTGTGCCTG CGACCAGATG TGGACAATCA
6301   CTGGGCACTC CGAGACTTTG CTGCCCGCCT GGTGGCCCAG ATCTGCAAGC ATTTTAGCAC
6361   AACCACTAAC AACATCCAGT CCCGGATCAC CAAGACCTTC ACCAAGAGCT GGGTGGACGA
6421   GAAGACGCCC TGGACGACTC GTTATGGCTC CATCGCAGGC TTGGCTGAGC TGGGACACGA
6481   TGTTATCAAG ACTCTGATTC TGCCCCGGCT GCAGCAGGAA GGGGAGCGGA TCCGCAGTGT
6541   GCTGGACGGC CCTGTGCTGA GCAACATTGA CCGGATTGGA GCAGACCATG TGCAGAGCCT
6601   CCTGCTGAAA CACTGTGCTC CTGTTCTGGC AAAGCTGCGC CCACCGCCTG ACAATCAGGA
6661   CGCCTATCGG GCAGAATTCG GGTCCCTTGG GCCCCTCCTC TGCTCCCAGG TGGTCAAGGC
6721   TCGGGCCCAG GCTGCTCTGC AGGCTCAGCA GGTCAACAGG ACCACTCTGA CCATCACGCA
6781   GCCCCGGCCC ACGCTGACCC TCTCGCAGGC CCCACAGCCT GGCCCTCGCA CCCCTGGCTT
6841   GCTGAAGGTT CCTGGCTCCA TCGCACTTCC TGTCCAGACA CTGGTGTCTG CACGAGCGGC
6901   TGCCCCACCA CAGCCTTCCC CTCCTCCAAC CAAGTTTATT GTAATGTCAT CGTCCTCCAG
6961   CGCCCCATCC ACCCAGCAGG TCCTGTCCCT CAGCACCTCG GCCCCCGGCT CAGGTTCCAC
7021   CACCACTTCG CCCGTCACCA CCACCGTCCC CAGCGTGCAG CCCATCGTCA AGTTGGTCTC
7081   CACCGCCACC ACCGCACCCC CCAGCACTGC TCCCTCTGGT CCTGGGAGTG TCCAGAAGTA
7141   CATCGTGGTC TCACTTCCCC CAACAGGGGA GGGCAAAGGA GGCCCCACCT CCCATCCTTC
7201   TCCAGTTCCT CCCCCGGCAT CGTCCCCGTC CCCACTCAGC GGCAGTGCCC TTTGTGGGGG
7261   GAAGCAGGAG GCTGGGGACA GTCCCCCTCC AGCTCCAGGG ACTCCAAAAG CCAATGGCTC
7321   CCAGCCCAAC TCCGGCTCCC CTCAGCCTGC TCCGCGGTCC GGTGGTGGTG GTGAAAACCT
7381   GTATTTTCAG GGCGAGTCTG GCAAGACGGC TTCTCCCAAG AGCATGCCGA AAGATGCACA
7441   GATGATGGCA CAAATCCTGA AGGATATGGG GATTACAGAA TATGAGCCAA GAGTTATAAA
7501   TCAGATGTTG GAGTTTGCCT TCCGATATGT GACCACAATT CTAGATGATG CAAAAATTTA
7561   TTCAAGCCAT GCTAAGAAAG CTACTGTTGA TGCAGATGAT GTGCGATTGG CAATCCAGTG
7621   CCGCGCTGAT CAGTCTTTTA CCTCTCCTCC CCCAAGAGAT TTTTTATTAG ATATTGCAAG
7681   GCAAAGAAAT CAAACCCCTT TGCCATTGAT CAAGCCATAT TCAGGTCCAA GGTTGCCACC
7741   TGATAGATAC TGCTTAACAG CTCCAAACTA TAGGCTGAAA TCTTTACAGA AAAAGGCATC
7801   AACTTCTGCG GGAAGAATAA CAGTCCCGCG GTTAAGTGTT GGTTCAGTTA CTAGCAGACC
7861   AAGTACTCCC ACACTAGGCA CACCAACCCC ACAGACCATG TCTGTTTCAA CTAAAGTAGG
7921   GACTCCCATG TCCCTCACAG GTCAAAGGTT TACAGTACAG ATGCCTACTT CTCAGTCTCC
7981   AGCTGTAAAA GCTTCAATTC CTGCAACCTC AGCAGTTCAG AATGTTCTGA TTAATCCATC
8041   ATTAATCGGG TCCAAAAACA TTCTTATTAC CACTAATATG ATGTCATCAC AAAATACTGC
8101   CAATGAATCA TCAAATGCAT TGAAAAGAAA ACGTGAAGAT GATGATGATG ACGATGATGA
8161   TGATGATGAC TATGATAATC TGCGGTCCGG CCACCATCAT CACCACCATT GATAAGCTAG
8221   CGGCCGCTTT CGAATCTAGA GCCTGCAGTC TCGACAAGCT TGTCGAGAAG TACTAGAGGA
8281   TCATAATCAG CCATACCACA TTTGTAGAGG TTTTACTTGC TTTAAAAAAC CTCCCACACC
8341   TCCCCCTGAA CCTGAAACAT AAAATGAATG CAATTGTTGT TGTTAACTTG TTTATTGCAG
8401   CTTATAATGG TTACAAATAA AGCAATAGCA TCACAAATTT CACAAATAAA GCATTTTTTT
8461   CACTGCATTC TAGTTGTGGT TTGTCCAAAC TCATCAATGT ATCTTATCAT GTCTGGATCT
8521   GATCACTGCT TGAGCCTAGG AGATCCGAAC CAGATAAGTG AAATCTAGTT CCAAACTATT
8581   TTGTCATTTT TAATTTTCGT ATTAGCTTAC GACGCTACAC CCAGTTCCCA TCTATTTTGT
8641   CACTCTTCCC TAAATAATCC TTAAAAACTC CATTTCCACC CCTCCCAGTT CCCAACGCCA
8701   ACTCCATGTG ACAAACCGTC ATCTTCGGCT ACTTT
```

RECOMBINANT EXPRESSION OF MULTIPROTEIN COMPLEXES USING POLYGENES

This application is a U.S. national stage of International Application No. PCT/EP2006/010608 filed Nov. 6, 2006.

The present invention relates to a recombinant polynucleotide encoding, each within a single open reading frame (ORF), at least two polygenes each coding for at least three biologically active polypeptides wherein at least two of the polypeptides encoded by the genes constituting the polygenes are of non-viral origin, at least two of the polypeptides encoded by the genes constituting the polygenes are each capable of at (east transiently interacting with at least one other polypeptide encoded by a gene of said polygenes, and the genes constituting each polygene are connected to one another by a sequence coding for at least one protease cleavage site and/or by a sequence coding for at least one self-cleaving peptide. Further embodiments of the present invention are a vector containing the recombinant polynucleotide, a host cell containing the recombinant polynucleotide and/or the vector and a non-human transgenic animal transformed with the recombinant polynucleotide and/or the vector. The present invention also relates to methods for the production of the polynucleotide and for the manufacture of multiprotein complexes. The embodiments of the present invention are particularly useful in gene therapy, drug candidate screening, vaccine production and crystallisation of multiprotein complexes for structural investigation.

An intense focus of biological research efforts in the post-genomic era is the elucidation of protein interaction networks (interactome). Since many of the identified multiprotein complexes are not present in sufficient quantities in their native cells for detailed molecular biological analysis, their study is dependent on recombinant technologies for large-scale heterologous protein production. Recombinant expression methods require a disproportionate investment in both labor and materials prior to multiprotein expression, and subsequent to expression do not provide flexibility for rapidly altering the multiprotein components for revised expression studies.

There are several recombinant technologies that are currently used to obtain multisubunit complexes. Proteins can for example be expressed in isolation in *E. coli* either in soluble form or as inclusion bodies, purified and then reconstituted with similarly produced proteins in vitro into multiprotein complexes. Eukaryotic cells (e.g. mammalian or yeast cells) can also be used as hosts in transient expression experiments. This methodology is entirely dependent on the existence of an efficient in vitro reconstitution protocol. While this strategy may yield acceptable results for more simple systems with small subunit sizes, it is generally not applicable for more complicated multiprotein complexes containing many, and also large, subunits (e.g. close to all higher eukaryotic—in particular human—regulatory complexes).

Co-expression has been recognised as a superior alternative to the strategy of in vitro reconstitution as outlined above. Several co-expression systems have been developed in the past both for prokaryotic and eukaryotic expression. In prokaryotic systems, co-expression can be achieved by generating a single plasmid containing all genes of choice or by co-transforming several plasmids containing one or two genes and different resistance markers and replicons.

Co-expression in eukaryotic cells has been realised by using the baculovirus system, initially with limited success by co-infection with several viruses, and later and more successfully by expressing all proteins from a single virus, offering many advantages and eliminating several limitations present in prokaryotic systems (such as comparatively small subunit sizes, lack of authentic processing, difficult expression of eukaryotic (especially human) proteins etc.). For the baculovirus system, expression from a single virus has been shown to increase yields dramatically (Berger et al. (2004) *Nature Biotech.* 22, 1583-1587; see also Comment (2004), *Nature Biotech.* 22, vii, New & Views (2004), *Nature Biotech.* 22, 152, Research Highlights, *Nature Methods* 2, 7 (2005); Bertolotti-Ciarlet et al. (2003) *Vaccine* 21, 3885-3900), while decisively reducing the logistic demands especially for large scale production.

A major improvement of multiprotein expression was the provision of the modular system for the generation of multigene expression cassettes provided by the present, inventors, which is disclosed in WO 2005/085456 A1 (PCT/EP2004/013381; see also Berger et al. (2004) ibid.). The MultiBac technology described in WO 2005/085456 A1 (PCT/EP2004/013381) enables the simple generation of multigene expression cassettes as well as modification and revision of expression experiments (Berger et al. (2004) ibid.).

However, a hindrance for successful expression and in vivo assembly of multisubunit complexes, in particular with many (6, 7, 8 or more), subunits (which constitute the majority of eukaryotic, e.g. human, gene regulatory complexes) is found in the fact that the relative expression levels of these subunits typically vary significantly based on in many cases not fully understood mechanisms (e.g. transcription and translation efficacy, protein stability, mRNA stability and secondary structures etc.): As a consequence, the subunit which is expressed in the least amount in an intrinsically unbalanced system will dictate the overall success of the multisubunit complex production experiment by limiting total complex yield. Accordingly, the transcription/translation machinery will produce excess amounts of other components which are not incorporated in the process thus "wasting" cellular transcription/translation resources. Individual expression levels typically vary several fold (e.g. up to 10 fold or more) with respect to each other, entailing losses which are refractory to a successful production of the desired multisubunit complexes, in particular in the case of complexes with more than 4; such as 5, 6, 8, 10 of more subunits (e.g. in the case of many eukaryotic gene regulatory complexes).

Viruses of the picornavirus super-group have a genome consisting of a single-stranded RNA molecule in sense orientation containing a single or two ORFs that code(s) for a polyprotein comprising the viral proteins which are connected to one another by cleavage sites of a viral protease or by self-cleaving peptides (reviewed, e.g., in Ryan et al. (1997) J. Gener. Virol. 78, 699-723).

The general concept of expressing a polyprotein through a recombinant virus for the production of protein complexes has been applied in the reconstitution of a TCR (T cell receptor): CD3 complex (Szymczak et al. (2004) Nature Biotech. 5, 589-594). The authors used two recombinant retroviral vectors wherein one vector contained the sequences encoding the two TCR subunits whereas the other vector encoded a polyprotein comprising the four CD3 subunits. The subunits were connected by self-cleaving 2A peptide sequences derived from aphthoviruses. One disadvantage of this approach is that, in order to reconstitute the complete complex, two separate vectors must be prepared and two transfections are necessary.

The viral polyprotein approach has been applied in baculovirus expression systems for small constructs such as heterodimeric IL-12 (Kokuho et al. (1999) Vet. Immunol. Immunopathol. 72, 289-302) and fusion proteins comprising a nuclear targeting signal derived from baculoviral polyhedrin and a protein of interest (U.S. Pat. No. 5,179,007).

Therefore, the technical problem underlying the present invention is to provide a new system for improved expression of multiple proteins.

The solution of the above technical problem is provided by the embodiments defined in the claims.

In particular, the present invention provides a polynucleotide encoding, each within a single open reading frame (ORF), at least two polygenes each coding for at least three biologically active polypeptides wherein at least two of the polypeptides encoded by the genes constituting the polygenes are of non-viral origin, at least two of the polypeptides encoded by the genes constituting the polygenes are each capable of at least transiently interacting with at least one other polypeptide encoded by a gene of said polygenes, and the genes constituting each polygene are connected to one another by a sequence coding for at least one protease cleavage site and/or by a sequence coding for at least one self-cleaving peptide.

The polynucleotide according to the present invention may be a DNA, RNA or a polynucleotide comprising one or more synthetic nucleotide analogues. The polynucleotide may be present in single or double stranded form, DNA, in particular double-stranded DNA, forms are especially preferred. The polynucleotide of the present invention may be produced by chemical synthesis. Preferred polynucleotide constructs of the present invention are made by recombinant gene technology (see, e.g., Sambrook et al. "Molecular Cloning", Cold Spring Harbor Laboratory, 1989).

A "polygene" as used herein is a nucleic acid sequence that encodes at least three biologically active polypeptides in a single ORF. Thus, each "gene" constituting the polygene is a nucleic acid sequence coding for a polypeptide, in particular a protein or fragment, variant, mutant or analogue thereof, having a specific, in particular structural, regulatory or enzymatic, function. Preferably the "gene" encoding the polypeptide comprises the coding region of a cDNA encoding the structural, regulatory or enzymatic protein or fragment, variant, mutant or analogue thereof.

A "fragment" of the polypeptide encoded by a gene contained in the polygenes means a part or region of the original polypeptide, preferably a fragment retaining at least one of the functions of the complete protein. A "variant" of the polypeptide encoded by a gene contained in the polygene means a polypeptide that is a functional or non-functional equivalent of the original polypeptide derived from another species or a functional or non-functional derivative of the original polypeptide that arises from alternative splicing or post-translational processing. A "mutant" of the polypeptide encoded by a gene contained in the polygene means a polypeptide that is derived from a naturally occurring protein by insertion, substitution, addition and/or deletion of one or more amino acid residues. An "analogue" of the polypeptide encoded by a gene contained in the polygene means functional equivalent of the original polypeptide that may even have a non-related amino acid sequence but exerts the same function as the polypeptide it is analogous to.

Correspondingly, on the nucleic acid level, a gene "fragment" is a part or region of the original gene the "fragment" is derived from. The gene "variant" has a sequence that is found in a different species compared to the original gene, or it may encode a splicing variant or post-translationally processed version of the polypeptide in question. The "mutant" is derived from the parent gene by insertion, substitution, addition and/or deletion of one or more nucleotides. The "analogue" of a gene encodes a functional equivalent of the polypeptide encoded by the parent gene.

At least two of the genes in the polygenes according to the present invention are of non-viral origin. "Non-viral" means that the nucleic acid sequence encoding the polypeptide (representing a functional protein or a fragment, variant, analogue or mutant thereof) is originally not found in or not derived from the genome of a virus. In particular, nucleotide sequences comprised in the polygene of the polynucleotide according to the present invention stem from eukaryotes and/or prokaryotes.

Thus, according to the present invention, the genes encoding the subunits (such as a multiprotein complex or members of a metabolic pathway or any other proteins that at least potentially interact at least transiently with one another) of a multisubunit assembly are present in at least two open reading frames (ORFs). The sequences encoding the subunits (polypeptides) of the assembly are present in at least two polygenes wherein the genes constituting each polygene are connected to one another by a sequence (there may be more than one) coding for a protease cleavage site (i.e. a sequence comprising the recognition site of a protease) or at least one self-cleaving peptide.

According to a preferred embodiment of the present invention the protease(s) capable of cleaving the cleavage; sites; encoded by the sequence(s) connecting the genes constituting the polygenes is/are encoded by the polynucleotide of the present invention. More preferably, the gene(s) encoding the protease(s) is/are part of at least one of the polygenes.

Suitable protease cleavages sites and self-cleaving peptides are known to the skilled person (see, e.g., in Ryan et al. (1997) J. Gener. Virol. 78, 699-722; Scymczak et al. (2004) Nature Biotech. 5, 589-594). Preferred examples of protease cleavage sites are the cleavage sites of potyvirus NIa proteases (e.g. tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, thrombin, factor Xa and enterokinase. Due to its high cleavage stringency, TEV (tobacco etch virus) protease cleavage sites are particularly preferred. Thus, the genes of the polygenes according to the present invention are preferably connected by a stretch of nucleotides comprising a nucleotide sequence encoding an amino acid sequence of the general, form EXXYXQ(G/S) wherein X represents any amino acid (cleavage by TEV occurs between Q and G or Q and S). Most preferred are linker nucleotide sequences coding for ENLYFQG and ENLYFQS, respectively.

Preferred self-cleaving peptides (also called "cis-acting hydrolytic elements", CHYSEL; see deFelipe (2002) Curr. Gene Ther. 2, 355-378) are derived from potyvirus and cardiovirus 2A peptides. Especially preferred self-cleaving peptides are selected from 2A peptides derived from FMDV (foot-and-mouth disease virus), equine rhinitis A virus, Thosea asigna virus and porcine teschovirus.

At least two of the polypeptides encoded by the polygenes of the present invention are capable of at least transiently interacting with one other polypeptide encoded by the polygenes, or they are at least suspected to be capable of at least transiently interacting with another polypeptide encoded by a gene contained in the polygenes. Typical "interactions" formed between the polypeptides include covalent binding, hydrogen bonds, electrostatic interactions and Van-der-Waals interactions. "Transient" interactions are common to biomolecules, in particular proteins, and are typically represented by interactions between enzymes and their substrates, receptors and their (agonistic or antagonistic) ligands, interactions between members of metabolic pathways and interactions between proteins of regulatory (e.g. gene regulatory) complexes.

The polypeptides encoded by the nucleotide sequences constituting the polygenes of the present invention may be the same or different. Thus, each polygene present in the constructs of the invention may contain one or more copy of each nucleotide sequence encoding a protein of interest. In this manner it is, e.g., possible to provide constructs that serve for optimal expression of the desired proteins, in particular in case proteins are normally expressed at different levels and/or are present in a macromolecular assembly in different stoichiometries. Therefore, in case a polypeptide is poorly expressed in commonly used systems, two or more copies of the corresponding coding sequence may be integrated into one or more polygene(s) of an inventive construct. The same approach may be used, in case a polypeptide is present as a dimer, trimer or multimer in a desired complex. In this manner, the constructs of the present invention may be assembled individually according to the requirements (expression levels, stoichiometry etc.) of any complex or other macromolecular assembly a person skilled in the art desires to express and/or to purify.

It is further preferred that the genes constituting the polygenes are selected from the group consisting of genes encoding members of multiprotein complexes and genes encoding members of metabolic pathways. Preferred multiprotein complexes are gene regulatory protein complexes such as transcription factor complexes, transport complexes such as complexes involved in nuclear and/or cellular transport, protein folding complexes, receptor/ligand complexes, cell-cell recognition complexes, complexes involved in apoptosis, complexes involved in cell cycle regulation etc. Members of metabolic pathways are, e.g. members of carbohydrate metabolism (such as glycolysis, gluconeogenesis, citric acid cycle, glycogen biosynthesis, galactose pathway, calvin cycle etc.), lipid metabolism (such as triacylglycerol metabolism, activation of fatty acids, β-oxidation of fatty acids (even chain/odd chain), α-oxidation pathway, fatty acid biosynthesis, cholesterol biosynthesis etc.), amino acid metabolism such as glutamate reactions, Krebs-Henseleit urea cycle, shikimate pathway, Phe and Tyr biosynthesis, Trp biosynthesis etc.), energy metabolism (such as oxidative phosphorylation, ATP synthesis, photosynthesis, methane metabolism etc.) nucleic acid metabolism (purin and pyrimidine biosynthesis and degradation, DNA replication etc.). Members of multiprotein complexes and members of metabolic pathway may be taken from, e.g. http://www.biocarta.com/genes/index.asp and G. Michal (ed.) Biochemical Pathways, 1. edition, John Wiley & Sons, Hoboken, N.J., USA, 1990, the disclosure content of which is hereby incorporated by reference.

Each polygene according to the present invention contains at least 3 genes, i.e. sequences encoding a biologically active polypeptide. More preferred are polygenes encoding 4, 5 6 or more or even more proteins. As mentioned above, it is preferred that the protease(s) capable of cleaving the protease cleavage sites connecting the polypeptides is/are encoded by at least one of the polygenes.

According to a preferred embodiment, the polynucleotide of the present invention contains at least two promoter sequences which are each operatively linked to one of the polygenes, thus capable of controlling the expression of the polygenes. Suitable promoters in the constructs of the present invention may be selected from the group consisting of polh, p10 and pXIV very late baculoviral promoters, vp39 baculoviral late promoter, vp39polh baculoviral late/very late promoter, $P_{cap/polh}$, pcna, etl, p35, da26 baculoviral early promoters; CMV, SV40, UbC, EF-1α, RSVLTR, MT, $P_{DS47}$, Ac5, $P_{GAL}$ and $P_{ADH}$. The promoter sequences may be the same for all polygenes, or different promoters may be selected for the different polygenes.

Preferably, the each ORF containing a polygene of the present invention is flanked by a terminator sequence such as SV40, HSVtk or BGH (bovine growth hormone).

The polynucleotide according the present invention may contain further regulatory sequences such as enhancers or suppressor sequences.

It is further preferred that the polynucleotide according to the present invention contains at least one site for its integration into a vector or host cell. Such an integration site will allow for the convenient genomic or transient incorporation of the polynucleotide into vectors (such as virus) and host cells (e.g., eukaryotic host cells), respectively. Sites for genomic integration are more preferred.

Especially preferred integration sites are those which are compatible for the polynucleotide's integration into a virus. More preferably, the integration site is compatible for the polynucleotide's integration into a virus selected from the group consisting of adenovirus, adeno-associated virus (AAV), autonomous parvovirus, herpes simple virus (HSV), retrovirus, rhadinovirus, Epstein-Barr virus, lentivirus, semliki forest virus and baculovirus.

In a further preferred embodiment, the integration site is compatible for the polynucleotide's integration into a eukaryotic host cell which may preferably be selected from the group consisting of mammalian (such as human cells, e.g. HeLa, Huh7, HEK293, HepG2, KATO-III, IMR32, MT-2, pancreatic β cells, keratinocytes, bone-marrow fibroblasts, CHP212, primary neural cells, W12, SK-N-MC, Saos-2, WI38, primary hepatocytes, FLC3, 143TK-, DLD-1, umbilical vein cells, embryonic lung fibroblasts, primary foreskin fibroblasts, osteosarcoma cells, MRC5, MG63 cells etc.), porcine (such as CPL; FS-13, PK-15) cells, bovine (such as MDB, BT) cells, ovine (such as FLL-YFT) cells, *C. elegans* cells, yeast (such as *S. cerevisiae, S. pombe, C. albicans, P. pastoris*) cells, and insect cells (such as *S. frugiperda*, e.g. Sf9, Sf21, Express Sf+, High Five H5 cells, *D. melanogaster*, e.g. S2 Schneider cells).

Particularly preferred integration sites are selected from the transposon elements of Tn7, λ integrase-specific attachment sites and SSRs (site specific recombinases), preferably the cre-lox specific (LoxP) site or the FLP recombinase specific recombination (FRT) site.

In a preferred embodiment of the present invention the polynucleotide additionally comprises one or more resistance markers for selecting host cells with desired properties based on a resistance to otherwise toxic substances. Examples of suitable resistance markers are those providing resistance against ampicillin, chloramphenicol, gentamycin, spectinomycin and/or kanamycin.

For its incorporation into a prokaryotic host cell, the polynucleotide of the present invention preferably comprises a conditional R6Kγ origin of replication for making propagation dependent on the pir gene in a prokaryotic host.

Especially preferred embodiments of the polynucleotide of the present invention result by the insertion of the polygenes as expression cassettes into constructs disclosed in WO 2005/085456 A1 (PCT/EP2004/013381).

Therefore, it is preferred that the polynucleotide of the present invention comprises a functional arrangement according to the following Formula I

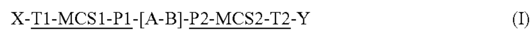

X-T1-MCS1-P1-[A-B]-P2-MCS2-T2-Y (I)

comprising (a) at least two expression cassettes T1-MCS1-P1 and P2-MCS1-T2 in a head-to-head, head-to-tail or tail-to-tail arrangement, each comprising a multiple cloning site MCS1 or MCS2, flanked by a promoter P1 and a terminator sequence T1 for MCS1 and flanked by a promoter P2 and a terminator sequence T2 for MCS2

(b) at least one multiplication module M in between the promoters P1 and P2 comprising at least two restriction sites A and B (c) at least two restriction sites X and Y each flanking one of the expression cassettes, wherein (i) restriction sites A and X as well as B and Y are compatible, but (ii) the ligation products of AY and BX are not enzymatically cleavable by restriction enzymes a, b, x or y specific for restriction sites A, B, X and Y, and (iii) restriction sites A and B as well as restriction sites X and Y are incompatible, wherein each polygene is inserted into one of the expression cassettes.

With respect to further preferred embodiments of the constructs having the arrangement of Formula (I) it is expressly referred to WO 2005/085456 A1 (PCT/EP2004/013381). In particular, restriction sites A and B in the multiplication module M are selected from the group consisting of restriction sites BstZ17I, SpeI, ClaI and NruI or restriction sites cleaved by isoschizomers thereof. Isoschizomers are restriction enzymes that have: identical cleavage sites. Furthermore, preferred examples of the restriction sites X and Y are restriction sites selected from the group consisting of PmeI and AvrII or restriction sites cleaved by isoschizomers thereof.

Particularly preferred polynucleotides having each polygene inserted into one of the expression cassettes contained in the above formula (I) comprise the following features:

(a) promoters P1 and P2 are selected from the group consisting of polh and p10;

(b) terminator sequences are selected from the group consisting of SV40 and HSVtk;

(c) restriction sites A and B in the multiplication module M are selected from group consisting of restriction sites BstZ171I, SpeI, ClaI and NruI;

(d) restriction sites X and Y are selected from the group consisting of restriction sites PmeI and AvrII; and (e) sites for virus integration are selected from the group consisting of cre-lox and Tn7.

With respect to the production of polynucleotides having the above arrangement according to Formula (I) it is expressly referred to WO 2005/085456 A1 (PCT/EP2004/013381).

The provision of polynucleotides of the present invention encoding several biologically active polypeptides within two or more ORFs each containing a polygene provides a major improvement with respect to the cloning and expression of genes coding for members of multisubunit protein complexes: On the one hand, assembly of all subunit genes into a single ORF is often impossible or highly difficult because of the huge size and numbers of coding sequences to be coupled. On the other hand, efficient assembly of several or all members of a multisubunit complex each present in separate expression cassettes has often turned out to be highly inefficient, since the overall complex yield is determined by the least expressed subunit. According to the present invention the subunits of a multiprotein assembly are encoded by at least two polygenes (each representing a single ORF) each coding for at least three polypeptides (preferably of non-viral origin) which results in an optimal compromise between manageability of the construct and its constituents (in particular assembly of the polygenes) and expression efficiency (in particular in case the polynucleotide of the present invention is present in a suitable vector).

Therefore, a further embodiment of the present invention is a vector containing the above-described polynucleotide. The vector may be selected from the group consisting of plasmids, expression vectors and transfer vectors. More preferably, the vector of the present invention is useful for eukaryotic gene transfer, transient or viral vector-mediated gene transfer.

Especially preferred vectors are eukaryotic expression vectors such as viruses selected from adenovirus, adeno-associated virus (AAV), autonomous parvovirus, herpes simple virus (HSV), retrovirus, rhadinovirus, Epstein-Barr virus, lentivirus, semliki forest virus and baculovirus. Most preferred vectors of the present invention are baculovirus expression vectors. Preferred baculovirus of the present invention are embodiments wherein the genes v-cath and chiA are functionally disrupted, since this leads to improved maintenance of cellular compartments during infection and protein expression. The v-cath gene encodes the viral protease V-CATH which is activated by upon cell death by a process dependent on a juxtaposed gene on the viral DNA, chiA, which codes for a chitinase. Both genes are preferably disrupted to eliminate V-CATH activity and to gain the option of utilising chitin affinity chromatography without interference form the chiA gene product. The quality of the expression products generated by a baculovirus system lacking functionally active v-cath and chiA genes is significantly improved because of the reduction of viral-dependent proteolytic activity and cell lysis.

Preferably, vectors according to the present invention comprise a site for SSRs, preferably LoxP for cre-lox site specific recombination. More preferably, the cre-lox site is located in one or both of the baculoviral gene v-cath and chiA so as to disrupt their function.

The vector of the present invention preferably contains one or more marker genes for selection of hosts successfully transfected with the correctly assembled vector. Examples of suitable marker genes are luciferase, β-Gal, CAT, genes encoding fluorescent proteins such as GFP, BFP, YFP, CFP and variants thereof, and the lacZα gene. The marker gene(s) may be functionally equivalent variants, mutants, fragments or analogues of the mentioned examples or other suitable markers known to the skilled person. Variants, mutants or analogues preferably show a homology of at least 75%, more preferably 85%, especially preferred 90%, in particular at least 95% on the amino acid level in comparison to the marker said variant, mutant or analogue is derived from.

In another preferred embodiment the vector of the present invention comprises a transposon element, preferably the Tn7 attachment site. More preferably, such a transposon element, e.g. the Tn7 attachment site, is located within a marker gene such that a successful integration by transposition can be assessed by testing the phenotype provided by the functional marker gene.

Preferred transfer vectors of the present invention are based on pFBDM or pUCDM as disclosed in WO 2005/085456 A1 (PCT/EP2004/13381; see SEQ ID NO: 1 and 2 as well as FIGS. 1 and 2, respectively disclosed therein). Further preferred transfer vectors of the present invention are based on derivatives of the above pFBDM and pUCDM, respectively, vectors:

Examples of particularly preferred derivatives of pFBDM and pUCDM are transfer vectors pSPL (FIG. 3), pFL (FIG. 4), pKL (FIG. 5) and pKDM (FIG. 6). Like pUCDM, pSPL contains a conditional origin of replication (R6Kγ). pFL (like pFBDM) contains a high copy-number replication origin (ColE1). pKDM and pKL have low-copy replication origins derived from pBR322. In analogy to pFBDM, pFL, pKL and pKDM contain transposon elements (Tn7R, Tn7L). Vectors pSPL, pFL and pKL have a LoxP imperfect inverted repeat flanking the dual expression cassette (as does pUCDM). All vectors contain the above-described multiplication module (M) for generating multigene cassettes1. pFL and pKL (and derivatives) are acceptor vectors, pUCDM and pSPL (and derivatives) are donor vectors in Cre-mediated plasmid fusions.

Important features of the above preferred examples of transfer vectors for generating the constructs of the present invention are summarised in the following Table 1.

TABLE 1

Features of preferred transfer vectors

| Vector | Antibiotic resistance marker | Replicon (source) | Host strain | Recombination and multiplication elements | Usage |
|---|---|---|---|---|---|
| pFBDM | Ampicillin Gentamycin | ColE1 | TOP10 * | Tn7L, Tn7R, multiplication module M | integration in MultiBac ** Tn7 site |
| pFL | Ampicillin Gentamycin | ColE1 | TOP10 | Tn7L, Tn7R, LoxP, multiplication module M | acceptor for plasmid fusions; integration in MultiBac ** Tn7 site |
| pKDM | Kanamycin Gentamycin | pBR322 | TOP10 | Tn7L, Tn7R, multiplication module M | integration in MultiBac ** Tn7 site |
| pKL | Kanamycin Gentamycin | pBR322 | TOP10 | Tn7L, Tn7R, LoxP, multiplication module M | acceptor for plasmid fusions; integration in MultiBac ** Tn7 site |
| pUCDM | Chloramphenicol | R6kγ | BW23473 | LoxP, multiplication module M | donor for plasmid fusions; integration in MultiBac ** LoxP site |
| pSPL | Spectinomycin | R6Kγ | BW23473 | LoxP, multiplication module M | donor for plasmid fusions; integration in MultiBac ** LoxP site |

* or any other general laboratory cloning strain ($recA^-$ $endA^-$ $pir^-$)
** see WO 2005/085456 A1

Therefore, the polygenes of the present invention are inserted into a vector such as pFBDM, pUCDM, pSPL, pFL, pKL or pKDM at the multiple cloning sites (MCS1 and MCS2), either by restriction enzyme cleavage and ligation or via recombination (e.g. using the BD In-Fusion enzyme). The baculovirus transfer vectors pFBDM, pUCDM, pSPL, pFL, pKL and pKDM comprise modified recipient baculovirus DNA engineered for improved protein production and allow for a simple and rapid method to integrate genes via two access sites (attTn7 and LoxP) into this baculoviral DNA in *E. coli* cells tailored for this purpose.

According to a further embodiment the present invention provides a host cell containing the polynucleotide and/or the vector of the invention.

Examples of preferred host cells are mammalian cells, such as human, rodent, porcine cells such as CPL, FS-13 and PK-15, bovine cells such as MDB and BT, ovine cells such as FLL-YFT, *C. elegans* cells, yeast cells such as *S. cerevisiae, S. pombe, P. pastoris* and *C. albicans*, insect cells such as cells from *S. frugiperda*, preferably Sf9, Sf21; Express Sf+ or High Five h5 cells, cells from *D. melanogaster* such as S2 Schneider cells, and bacteria such as *E. coli*, preferably strains Top10, Dh5α, DH10α, HB101, TG1, BW23473 and BW23474.

Preferred human cells are selected from HeLa, Huh7, HEK293, HepG2, KATO-III, IMR32, MT-2, pancreatic β cells, keratinocytes, bone-marrow fibroblasts, CHP212, primary neural cells; W12, SK-N-MC, Saos-2, WI38, primary hepatocytes, FLC3, 143TK-, DLD-1, umbilical vein cells, embryonic lung fibroblasts, primary foreskin fibroblasts, osteosarcoma cells, MRC5 and MG63 cells.

Host cells comprising a polynucleotide and/or vector according to the invention may be isolated cells or they may be present in tissues or organs.

A further embodiment of the present invention relates to a non-human transgenic animal being transformed with at least one polynucleotide sequence and/or vector of the invention. Preferred transgenic animals are rodent, porcine, bovine and *C. elegans* species.

The transgenic animal of the present invention is particularly useful for the elucidation of the role of multiprotein complexes or for screening of compounds for their biological activities in vivo.

A further embodiment of the present invention is a method for the production of the polynucleotide as defined above comprising the steps of:

(a) providing, preferably amplifying, the coding regions of the genes constituting the at least two polygenes;
(b) providing said coding regions with the sequences coding for the at least one protease cleavage site and/or the at least one self-cleaving peptide; and
(c) assembling the fragments resulting from steps (a) and (b) such that a single ORF results in each polygene; and
(d) combining the at least two polygenes into a single polynucleotide.

Another aspect of the invention is a method, for the production of the vector according to the present invention comprising the steps of (a) generating at least two polygenes each comprising at least three genes within a single ORF as defined above (preferably by the above method for the production of the polynucleotide of the present invention); and
(b) cloning the polygenes into a plasmid or viral vector, wherein at least one of the genes, of each polygene is of non-viral origin and at least two of the polypeptide encoded by; the genes are capable of at least, transiently interacting with one other polypeptide encoded by the genes.

Preferably, one of the genes assembled into the polygenes, is a gene encoding a protease capable of cleaving the protease cleavage sites connecting the polypeptides encoded by the polygenes. Preferred proteases are as defined above.

The construction of the polygenes as well as the vectors of the present invention can be carried out through various molecular biological techniques which are generally known to a person skilled in the art (see, e.g., Ausubel et al. (eds.) Current Protocols in Molecular Biology, John Wiley & Sons, Hoboken, N.J., USA, 2003). The production of a polygene may be earned out, e.g. by PCR amplification of the nucleotide sequences coding for the particular polypeptides (e.g. using corresponding cDNA templates), preferably by usage of a primer (either 5' or 3') providing the sequence(s) coding for the at least one protease cleavage site and/or the at least one self-cleaving peptide. Preferably, the primers further contain a recognition sequence of a suitable restriction enzyme. Preferably, each primer contains a restriction site that is different from the restriction site of the other primer such that a directional ligation of the resulting amplification product with another amplification product and/or a linearised vector containing the same restriction sites is possible. According to another preferred embodiment for the production of constructs by directional ligation, the primers may contain a recognition sequence of a restriction enzyme that produces an overhang which is not self-ligatable such as RsrII or BstEII. In case the primers themselves do not contain a restriction site, it is also possible to provide the amplification products with adapters comprising the desired restriction site(s). Of course, it is also possible to provide the coding regions for the desired polypeptides using any source (besides amplification). For example, the required sequences may be already present as such or in corresponding vectors from which the sequences may be cut out by appropriate restriction enzymes. Constructs that do not contain appropriate restriction sites etc. may be provided with the appropriate sequences (restriction site(s), protease cleavage site (s)/self-cleavable peptide(s), linkers etc.) by ligation of suitable adapters containing the required elements. The amplification products of any other appropriate construct (containing the restriction sites) are then cut with the appropriate restriction enzymes. Of course, the sequences of any primers used are preferably selected such that after final assembly of the polygenes, preferably into a suitable vector; a single ORF results for each polygene.

According to a preferred embodiment of the invention, the amplification products or other appropriate sequences may then be ligated sequentially or simultaneously into a suitable vector, e.g. at MCS1 or MCS2 of the MultiBac vector system referred to above. For example, one polygene may be introduced into pFDBM and another polygene may be ligated into pUCDM (as described in WO 2005/085456 A1 (PCT/EP2004/013381)). The resulting constructs are then used for the production of corresponding bacmids by cre-lox site-specific recombination (pUCDM derivative) and Tn7 specific transposition (pFBDM derivative) yielding a baculoviral expression vector ready for infection of corresponding insect cells for expression and purification of the multiprotein complex of interest.

Besides producing the polygenes and introducing these into a suitable vector by restriction/ligation it is also possible to assemble such constructs by homologous recombination using appropriate recombinases. Suitable examples of recombinase-based cloning techniques are the In-Fusion® system available from BD Biosciences Clontech, Heidelberg, Germany (see *Clontechniques*, October 2002, p. 10) and the Red®/ET® recombination system available from Gene Bridges GmbH, Dresden, Germany (see WO-A-99/29837; http://www.genebridges.com).

The In-Fusion® system requires 15 bp homologous regions in a DNA molecule to be fused into a linear construct (such as an appropriate vector) having the corresponding homologous regions. Accordingly, a vector containing a polygene of the present invention may assembled sequentially or simultaneously by providing the constituting coding regions (together with the linker sequences coding for a protease cleavage site and/or a self-cleaving peptide) with appropriate homologous sequences of 15 bp. If desired, the 15 bp homologous sequences may be selected such that the constituting coding regions are assembled in a desired order. Of course, appropriate homology regions may be introduced by PCR amplification of the corresponding fragments using primers containing the desired sequences.

The Red®/ET® recombination system, is different from the In-Fusion® system in that homology sequences of 40 to 60 base pairs are required, but the construct in which a fragment is to be inserted needs not to; be linear. The recombination is carried out in vivo in a host, preferably an *E. coli* strain, expressing the dual recombinase system "ET" (RecE/RecT of Redα/Redβ). Thus; the fragments constituting the polygenes may be directly transformed together with an appropriate vector into the appropriate host preferably *E. coli* cells. In this manner, each polygene may be assembled in the suitable vector either sequentially fragment by fragment (preferably comprising the coding region for each member polypeptide of the multiprotein complex+ at least one protease cleavage site sequence/self-cleaving peptide sequence), or by simultaneous transformation of all fragments.

Especially preferred polynucleotide constructs of the present invention contain polygenes of at least similar length, since the inventors have found that the expression of corresponding polyproteins from such constructs results in comparable expression levels. According to the present invention "polygenes of similar length" means that the lengths of the nucleotide sequences of the polygenes differ from one another by not more than 50%, more preferably not more than 30%, in particular not more than 20% or even less.

Furthermore, the present invention provides a method for the production of multiprotein complexes in vitro comprising the steps of (a) cultivating the host cell according to the present invention in a suitable medium under conditions allowing the expression of the polygenes; and
(b) recovering the expression products encoded by the polygenes from the medium and/or the host cells.

The present invention also relates to a method for the production of multiprotein complexes in vivo comprising the steps of (a) generating at least two polygenes each comprising at least three genes within a single ORF as defined above; and
(b) transforming the polygenes into an animal such that the polygenes are expressed in said animal.

Preferably the transformation of the animal with the polygenes according to step (b) is effected by means; of a vector, in particular; a viral-vector, more preferably a baculovirus vector. Baculoviruses are especially useful vehicles for delivery of polygenes into mammalian species. The above in vivo method is preferably carried out in mammals, *C. elegans* or insects. Particularly preferred examples of suitable animal species are defined herein above.

The embodiments of the present invention are also useful for the preparation of vaccines directed against multisubunit assemblies of proteins. Complexes of multiple subunits often display different epitopes compared to the individual proteins, constituting the complexes. Therefore, the multiprotein complexes produced according to the present invention display the naturally occurring relevant epitopes in a more appropriate fashion, thus providing better antigen targets for antibody production.

Recently, virion-like particles (VLPs) consisting of four proteins from the sever acute respiratory syndrome (SARS) coronavirus were made using a recombinant baculovirus expression vector (cf. Mortola et al. (2004), *FEBS Lett.* 576, 174-178). The effective expression of such infectious particles for the preparation of vaccines will be greatly facilitated using the polygene expression system according to the present invention. In particular, the high-yield expression of multisubunit assemblies that contain substantially more polypeptide than the example of SARS-VLPs is made available by the expression tools of the present invention.

Therefore, the present invention further relates to a method for the production of a vaccine comprising the steps of (a) administering at least one polynucleotide and/or vector of the present invention to a mammal, whereby the polygene of the invention is expressed within the mammal;
(b) optionally administering an adjuvants to the mammal; and
(c) optionally isolating the antibodies and/or spleen Cells producing antibodies specific for at least one of the polypeptide encoded by the polygenes.

The present invention provides a convenient and simple approach for the recombinant production of multiprotein assemblies, these multisubunit assemblies may be tested for protein complex interactions or modifications of the proteins constituting the multisubunit assembly. The multisubunit assemblies produced according to the present invention may also be assayed for their interaction with candidate compounds (small organic molecules, nucleic acids, peptides, polypeptides etc.) that may exert a biologically significant activity being of medical value.

Therefore, the present invention is also directed to a method for assaying protein complex interactions or protein modifications.

According to a preferred embodiment, the present invention provides a method for the screening of protein complex interactions or modifications of multiprotein complexes in vitro comprising the steps of (a) providing a host cell according to the present invention containing at least two polygenes;
(b) maintaining the host cell under conditions that allow expression of the polygenes; and
(c) detecting interactions between or modifications of the polypeptides encoded by the polygenes.

Another preferred embodiment of the present invention is a method for in vitro screening of candidate compounds capable of (i) interacting with a multiprotein complex and/or (ii) modification of proteins within a multiprotein complex and/or (iii) inhibiting interactions within or between multiprotein complexes and/or inhibiting modifications of proteins within a multiprotein complex, comprising the steps of (a) providing a host cell according to the present invention containing at least two polygenes;
(b) maintaining the host cells under conditions that allow expression of the polygenes;
(c) contacting a candidate compound with the host cell; and
(d) detecting interactions of the expression products with the candidate compound and/or interactions between the expression products and/or modifications of the expression products and/or inhibition of interactions between the expression products.

The polynucleotides and/or vectors of the present invention are also suitable for the screening of protein-protein, protein-(multi)protein complex or multiprotein complex-multiprotein complex interactions or modifications (phosphorylation, glycosylation etc.) of multiprotein complexes in vivo.

Thus, a further preferred embodiment of the present invention is a method for in vivo screening of candidate compounds capable of (i) interacting with a multiprotein complex and/or (ii) modification of proteins within a multiprotein complex and/or (iii) inhibiting interactions within or between multiprotein complexes and/or inhibiting modifications of (a) proteins within a multiprotein complex, comprising the steps of (a) providing an animal comprising at least one polynucleotide and/or vector of the invention containing at least two polygenes as defined above, whereby the polygenes are expressed in the animal;
(b) administering a candidate compound to the animal; and
(c) detecting interactions of the expression products with the candidate compound and/or interactions between the expression products and/or modifications of the expression products and/or inhibition of interactions between the expression products.

The multiprotein expression tools of the present invention are also of medical use. In particular, bioactive multiprotein complexes as well as medically advantageous combinations of proteins, e.g. antibody mixtures, optionally in combination with interleukins and/or adjuvants can be administered to an animal or human by means of the polynucleotides and/or the gene delivery vectors of the present invention.

Accordingly, the present invention further relates to the use of the polynucleotide and/or the vector and/or the host cell described above for the preparation of a medicament comprising a polygene transfer vehicle for gene therapy.

Tremendous efforts are being made to develop gene delivery systems for therapeutic applications. Gene therapy has been the focus of intense, enthusiasm but also criticism in the past to date, major progress has been made in evaluating gene therapy in clinical trials on the way to achieving safe/and applicable clinical in vivo and ex vivo strategies for human diseases (see Worgall S. (2004) *Peadiatr. Nephrol.*). Overall, gene; therapy now stands as a very promising avenue for the correction of genetic as well as acquired disorders entailing permanent or transient expression of a therapeutic gene product (Worgall S., ibid.). Recombinant vectors based on virus, in particular those that are not replication competent in mammalian hosts (e.g. baculoviral vectors) have emerged recently as a powerful tool for mammalian cell gene delivery and have been successfully applied to a whole range of mammalian cell lines including human, primate, rodent, bovine, procine and ovine cells (reviewed in Kost and Condreay (2002) *Trends Biotech.* 20, 173-180): To obtain complex gene transfer/therapy effects, both ex vivo and in vivo, an increasing demand has arisen for polycistronic viral vectors to accomplish more powerful results rather by combined gene therapy than by single gene therapy (de Felipe (2002), *Curr. Gene Ther.* 2, 355-378; Planelles (2003) *Meth. Mot. Biol.* 229, 273-284). The requirement for the incorporation of accessory genes into a carrier virus that is to be administered in vivo, e.g. to block inactivation by the complement system, has also been demonstrated by using a pseudotyped baculovirus with baculoviral gp64 envelope proteins that carried a human decay-accelerating factor protein domain fusion (Hueser et al. (2001) *Nat. Biotech.* 19, 451-455), exemplifying the necessity to provide recombinant modifications on the virus production level in addition to the multiple genes to be transferred for therapeutic purposes.

Accordingly, recombinant baculovirus of the present invention are preferred for preparing gene therapeutic medicaments. More preferably, the vector used for the medicament of the present invention is a baculovirus comprising at least two polygenes as defined above encoding (i) one or more therapeutic polypeptide(s) and (ii) one or more baculoviral proteins In a preferred embodiment, the protein(s) according to (ii) are humanised baculoviral proteins expressed from pseudotyped baculovirus, preferably a humanised baculovirus envelope protein gp64, e.g. gp64 fused with a human protein such as for example decay accelerating factor.

Furthermore, the present invention relates to an in vivo gene therapeutic method comprising the steps of (a) providing a polygene transfer vehicle comprising a polynucleotide according to the invention; and (b) administering the polygene transfer vehicle to a patient suffering from a genetic disorder.

The present invention further provides an ex vivo gene therapeutic method comprising the steps of (a) collecting cells of a patient suffering from a genetic disorder;

(b) transforming the collected cells with a polygene transfer vehicle comprising a polynucleotide according to the present invention; and (c) administering the transformed cells to the patient.

The multiprotein complexes produced according to the present invention may advantageously be used in biophysical studies, in particular structural studies using crystallographical, electron-microscopical and/or NMR techniques, protein chemical studies, in particular for protein-protein interactions, and for drug development.

Thus, the present invention is directed to the use of the polynucleotide and/or the vector and/or the host cell of the present invention for the crystallisation of multiprotein complexes.

A further embodiment of the present invention is a kit for the preparation of multiple-protein complexes comprising (a) primers for PCR amplification of the coding sequences constituting the polygenes;

(b) a plasmid or viral vector; and (c) optionally host cells suitable for the propagation of the plasmid or vector The primers are conveniently designed to match the needs for producing a single ORF for each polygene and may contain restriction sites for ligation (sequentially or simultaneously) into the plasmid or viral vector and/or the primers may contain sequences for assembling the polygenes and/or insertion into the plasmid or viral vector by homologous recombination (e.g. using the In-Fusion® system or Red®/ET® system as described above).

The Figures show:

FIG. 1 shows the nucleotide sequence (SEQ ID NO: 1) and deduced amino acid sequence (SEQ ID NO: 2) of a PCR product coding for human TATA-Box-Binding Protein (hTPB) core (hTBPc, c-terminal fragment of the full-length protein truncated at position 159). Positions of RsrII restriction sites (present in the primer sequences) are indicated.

FIG. 2 shows photographs of agarose gel electrophoretic analyses of in vitro ligation of hTBPc gene segments and subcloning of the mixture. The PCR-amplified hTPBc gene was digested by RsrII and purified (lane 1). Incubation with ligase yields a ladder of concatamers containing 1, 2, 3 and more genes linked in one ORF each (lane 2, lane 3 is MBI DNA Marker 1 kb ladder). Subcloning of the mixture of the thus-yielded expression constructs containing one polygene each with differing numbers of linked hTBPc genes that can be liberated by restriction digest using RsrII (lanes 4-7). Digestion outside of the inserted polygene evidences 1 (lane 8), 2 (lane 9), 3 (lane 10) and 5 (lane 11) hTBPc genes that yielded a single ORF in each case.

FIG. 8 shows the nucleotide sequence of pFBDO[hTBPc]3 (SEQ ID NO: 3).

FIG. 12 shows the nucleotide sequence of pFBDO [HisTEVTAF6TAF9]his (SEQ ID NO: 5).

The present invention is further illustrated by the following non-limiting examples.

EXAMPLES

Example 1

Production of Polygenes and Ligation into Expression Vectors

The principle of generating polygenes is shown here by using human TATA-Box-Binding protein (hTBP) core (hTBPc, c-terminal fragment of the full-length protein truncated at position 159). The gene encoding hTBPc was amplified by polymerase chain reaction (PCR) using a sense primer annealing to the 5' end of the gene containing an overhang possessing a RsrII restriction site and further encoding an amino acid spacer and a Tobacco-Etch-Virus (TEV) cleavage site. The antisense primer annealed to the 3' terminus of the gene and contained an RsrII restriction site. RsrII is a restriction enzyme that produces an asymmetric overhang of 3 nucleotides which do not self ligate, therefore, the restriction product is asymmetric and ligation yields a directional product. The PCR product/was digested with RsrII and purified. The DNA (SEQ ID NO: 1) and deduced amino acid sequence (SEQ ID NO: 2) of the PCR product are shown in FIG. 1.

Figure 2:
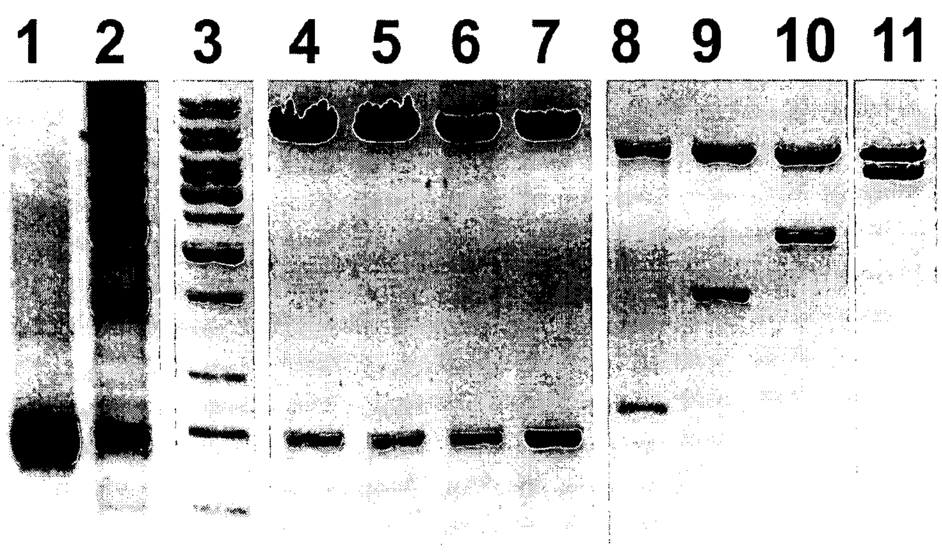
Figure 3:
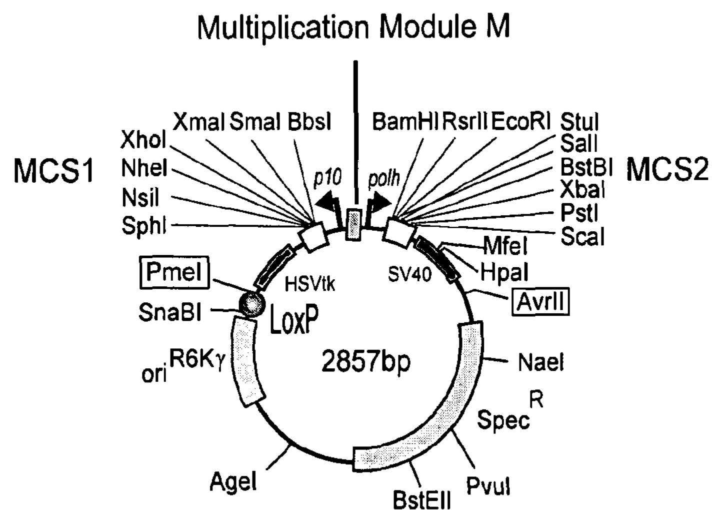
FIG. 3 shows a schematic representation of the basic transfer vector pSPL underlying preferred transfer vector constructs of the present invention.
Figure 4:
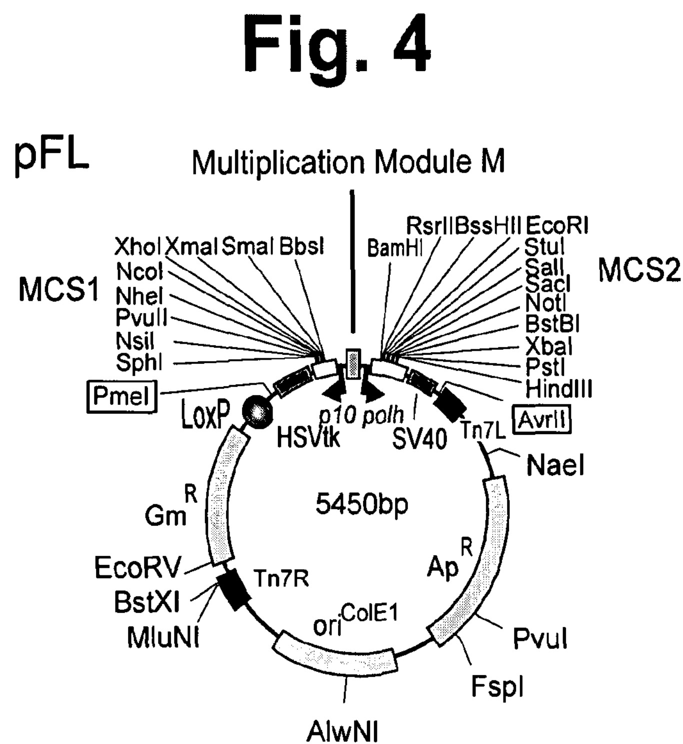
FIG. 4 shows a schematic representation of the basic transfer vector pFL underlying preferred transfer vector constructs of the present invention.
Figure 5:
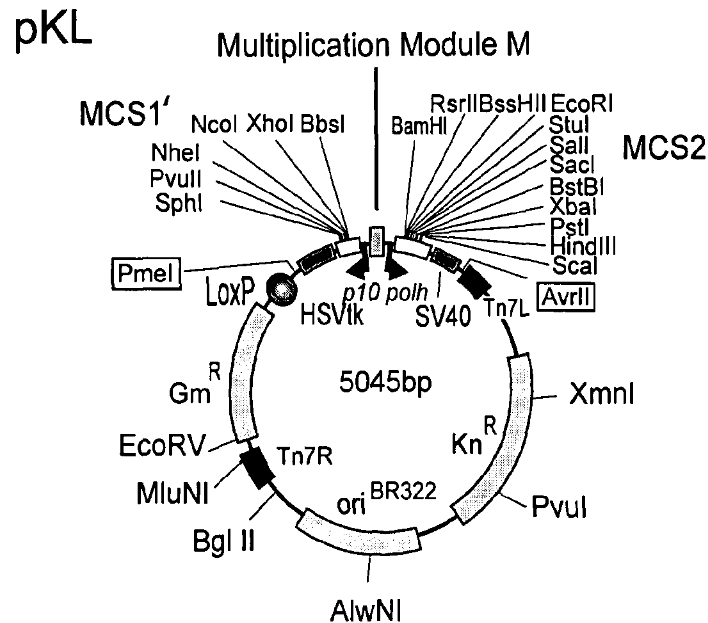
FIG. 5 shows a schematic representation of the basic transfer vector pKL underlying preferred transfer vector constructs of the present invention.
Figure 6:
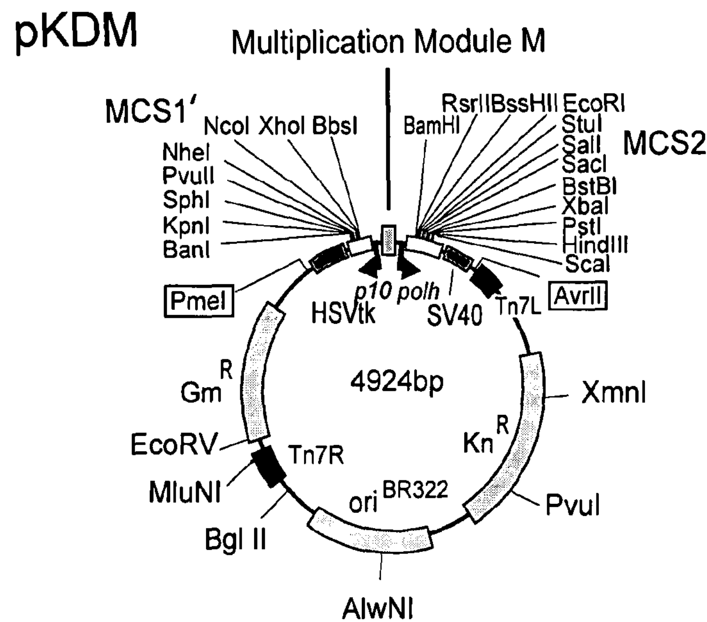
FIG. 6 shows a schematic representation of the basic transfer vector pKDM underlying preferred transfer vector constructs of the present invention.
Figure 7:
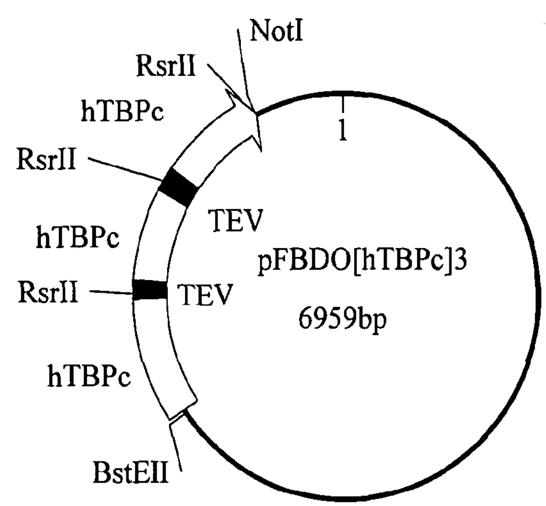
FIG. 7 shows a schematic representation of the transfer vector construct pFBDO[hTBPc]3.

Ligation yielded concatamers of hTBPc as shown in FIG. 2. Subcloning of the in vitro ligation reaction mixture into an appropriate vector yielded expression constructs containing polygenes encoding 1, 2, 3, and 5 hTBP proteins in a single polyprotein separated by TEV protease cleavage sites. A schematic representation and the nucleotide sequence (SEQ ID NO: 3) of one of the resulting expression vectors (pFBDO[hTBPc]3) are shown in FIGS. 3 and 4, respectively.

Example 2

Figure 9:
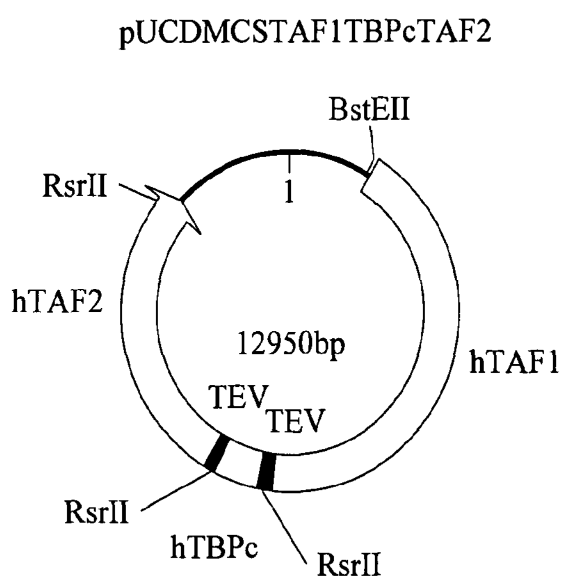
FIG. 9 shows a schematic representation of the transfer vector construct pUCDMCSTAF1TBPcTAF2.
Figures 10, 11:
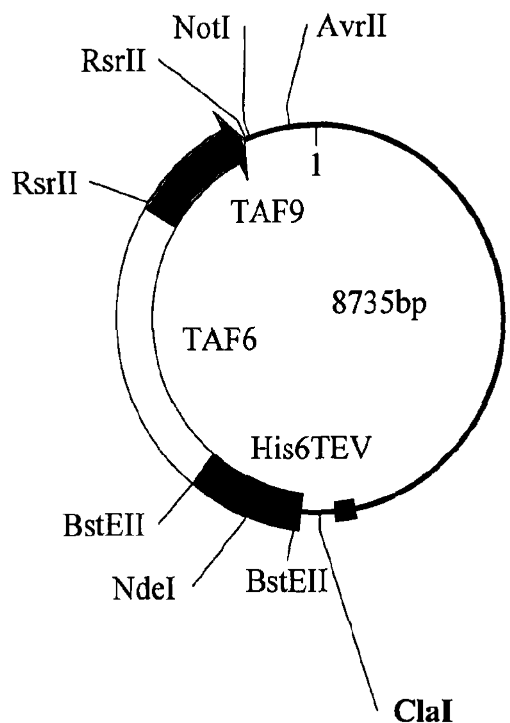
FIG. 10 shows the nucleotide sequence of pUCDMCSTAF1TBPcTAF2 (SEQ ID NO: 4).
FIG. 11 shows a schematic representation of the transfer vector construct pFBDO[HisTEVTAF6TAF9]his.

Generation of Baculoviral Transfer Vectors Containing Polygenes Encoding Subunits of a Human General Transcription Factor A polygene was generated encoding a polyprotein comprising human TBP associated factors hTAF1 and hTAF2 in addition to hTBPc inserted into a transfer vector pUCDM (see WO 2005/085456 A1 (PCT/EP2004/013381)) for baculovirus expression, with the genes separated by sequences encoding an amino acid spacer and a TEV protease site. A schematic representation of the resulting construct pUCDMCSTAF1TBPcTAF2 is shown in FIG. 9. The nucleotide sequence of the construct is shown in FIG. 10 (SEQ ID NO: 4). A further construct was generated containing a polygene encoding a polyprotein comprising TEV protease and human TBP associated factors hTAF6 and hTAF9 inserted into the transfer vector pFBDM (see WO 2005/085456 A1 (PCT/EP2004/013381)) for baculovirus expression, with the genes separated by sequences encoding an amino acid spacer and a TEV protease site. A schematic representation of the resulting construct pFDDO [HisTEVTAF6TAF9]his is shown in FIG. 11. The nucleotide sequence of this construct is shown in FIG. 12. (SEQ ID NO: 5)

Example 3

Preparation of Bacmid Constructs, Infection of Insect Cells and Protein Expression For the construction of bacmids constructs comprising the above two polygenes, the constructs pUCDMCSTAF1TBPcTAF2. (pUCDM derivative) and pFDDO[HisTEVTAF6TAF9]his (pFBDM derivative) were each introduced into DH10MultiBac$^{Cre}$ cells as described in Examples 5 (for pUCDMCSTAF1TBPcTAF2; Cre-lox site-specific recombination) and 6 (for pFDDO [HisTEVTAF6TAF9]his; Tn7 transposition) of WO 2005/085456 A1 (PCT/EP2004/013381). If desired, one-step transposition/cre-lox site-specific, recombination can be earned DH10MultiBac$^{Cre}$ cells as described in WO 2005/085456 A1 (PCT/EP2004/013381) as well. Bacmid preparation, infection of insect cells and protein expression was carried out according to established protocols (see, e.g., O'Reilly et al. (1994) "Baculovirus expression vectors. A laboratory manual" Oxford University, Press, New York—Oxford; "Bac-to-Bac™ Baculovirus Expression Systems Manual" Invitrogen, Life Technologies, Inc., 2000).

The following Sequence Listing is part of the present description, wherein the sequences are as follows:

SEQ ID NO: 1 is the nucleotide sequence of the PCR product coding for human TATA-Box-Binding Protein (hTPB) core (hTBPc, c-terminal fragment of the full-length protein truncated at position 159) shown in FIG. 1.

SEQ ID NO: 2 is the amino acid sequence of the human TATA-Box-Binding Protein core (hTBPc) shown in FIG. 1.

SEQ ID NO: 3 is the nucleotide sequence of pFBDO [hTBPc]3 shown in FIG. 8.

SEQ ID NO: 4 is the nucleotide sequence of pUCDMCSTAF1TBPcTAF2 shown in FIG. 10.

SEQ ID NO: 5 is the nucleotide sequence of pFBDO [HisTEVTAF6TAF9]his shown in FIG. 12.

The invention claimed is:

1. A polynucleotide encoding at least two polygenes, wherein each polygene has a single open reading frame (ORF), each polygene comprises at least three genes each coding for a biologically active polypeptide, at least two of the biologically active polypeptides encoded by any genes of the at least two polygenes are of non-viral origin, at least two of the biologically active polypeptides encoded by any genes of the at least two polygenes are each capable of at least transiently interacting with at least one of the other biologically active polypeptides, and the genes constituting each polygene are connected to one another by a sequence coding for at least one self-cleaving peptide, and at least one polygene comprises more than one copy of a gene coding for a biologically active polypeptide, wherein the genes constituting at least one polygene are further connected to one another by a sequence coding for at least one protease cleavage site.

2. The polynucleotide of claim 1, wherein the protease cleavage site is selected from the group consisting of a potyvirus NIa protease cleavage site, a potyvirus HC protease cleavage site, a potyvirus P1 (P35) protease cleavage site, a byovirus NIa protease cleavage site, a byovirus RNA-2-encoded protease cleavage site, an aphthovirus L protease cleavage site, an enterovirus 2A protease cleavage site, a rhinovirus 2A protease cleavage site, a picorna 3C protease cleavage site, a comovirus 24K protease cleavage site, a nepovirus 24K protease cleavage site, a rice tungro spherical virus 3C-like protease cleavage site, aparsnip yellow fleck virus 3C-like protease cleavage site, a thrombin cleavage site, a factor Xa cleavage site and an enterokinase cleavage site.

3. The polynucleotide of claim 2, wherein the protease cleavage site is a tobacco etch virus protease cleavage site.

4. The polynucleotide of claim 1, further comprising a gene encoding a protease capable of cleaving the protease cleavage site.

5. A host cell comprising the polynucleotide of claim 1.

* * * * *

SEQUENCE LISTING

```
<160> NUMBER OF SEQ ID NOS: 5

<210> SEQ ID NO 1
<211> LENGTH: 607
<212> TYPE: DNA
<213> ORGANISM: Artificial Sequence
<220> FEATURE:
<223> OTHER INFORMATION: Sythetic Construct; PCR product coding for
      hTBPc

<400> SEQUENCE: 1

cgaattcctc gagcggtccg gaggtaacgg atccgaaaac ctgtattttc agggttctgg     60
```

```
gattgtaccg cagctgcaaa atattgtatc cacagtgaat cttggttgta aacttgacct    120

aaagaccatt gcacttcgtg cccgaaacgc cgaatataat cccaagcggt ttgctgcggt    180

aatcatgagg ataagagagc cacgaaccac ggcactgatt ttcagttctg ggaaaatggt    240

gtgcacagga gccaagagtg aagaacagtc cagactggca gcaagaaaat atgctagagt    300

tgtacagaag ttgggttttc cagctaagtt cttggacttc aagattcaga acatggtggg    360

gagctgtgat gtgaagtttc ctataaggtt agaaggcctt gtgctcaccc accaacaatt    420

tagtagttat gagccagagt tatttcctgg tttaatctac agaatgatca aacccagaat    480

tgttctcctt atttttgttt ctggaaaagt tgtattaaca ggtgctaaag tcagagcaga    540

aatttatgaa gcatttgaaa acatctaccc tattctaaag ggattcagga agacgacgcg    600

gtccggc                                                              607
```

<210> SEQ ID NO 2
<211> LENGTH: 196
<212> TYPE: PRT
<213> ORGANISM: Homo sapiens

<400> SEQUENCE: 2

```
Arg Ser Gly Gly Asn Gly Ser Glu Asn Leu Tyr Phe Gln Gly Ser Gly
1               5                   10                  15

Ile Val Pro Gln Leu Gln Asn Ile Val Ser Thr Val Asn Leu Gly Cys
            20                  25                  30

Lys Leu Asp Leu Lys Thr Ile Ala Leu Arg Ala Arg Asn Ala Glu Tyr
        35                  40                  45

Asn Pro Lys Arg Phe Ala Ala Val Ile Met Arg Ile Arg Glu Pro Arg
    50                  55                  60

Thr Thr Ala Leu Ile Phe Ser Ser Gly Lys Met Val Cys Thr Gly Ala
65                  70                  75                  80

Lys Ser Glu Glu Gln Ser Arg Leu Ala Ala Arg Lys Tyr Ala Arg Val
                85                  90                  95

Val Gln Lys Leu Gly Phe Pro Ala Lys Phe Leu Asp Phe Lys Ile Gln
            100                 105                 110

Asn Met Val Gly Ser Cys Asp Val Lys Phe Pro Ile Arg Leu Glu Gly
        115                 120                 125

Leu Val Leu Thr His Gln Gln Phe Ser Ser Tyr Glu Pro Glu Leu Phe
    130                 135                 140

Pro Gly Leu Ile Tyr Arg Met Ile Lys Pro Arg Ile Val Leu Leu Ile
145                 150                 155                 160

Phe Val Ser Gly Lys Val Val Leu Thr Gly Ala Lys Val Arg Ala Glu
                165                 170                 175

Ile Tyr Glu Ala Phe Glu Asn Ile Tyr Pro Ile Leu Lys Gly Phe Arg
            180                 185                 190

Lys Thr Thr Arg
        195
```

<210> SEQ ID NO 3
<211> LENGTH: 6959
<212> TYPE: DNA
<213> ORGANISM: Artificial Sequence
<220> FEATURE:
<223> OTHER INFORMATION: Synthetic Construct; Plasmid pFBDO[hTBPc]3

<400> SEQUENCE: 3

```
ttctctgtca cagaatgaaa atttttctgt catctcttcg ttattaatgt ttgtaattga     60
```

```
ctgaatatca acgcttattt gcagcctgaa tggcgaatgg gacgcgccct gtagcggcgc    120
attaagcgcg gcgggtgtgg tggttacgcg cagcgtgacc gctacacttg ccagcgccct    180
agcgcccgct cctttcgctt tcttcccttc ctttctcgcc acgttcgccg gctttccccg    240
tcaagctcta aatcgggggc tccctttagg gttccgattt agtgctttac ggcacctcga    300
ccccaaaaaa cttgattagg gtgatggttc acgtagtggg ccatcgccct gatagacggt    360
ttttcgccct ttgacgttgg agtccacgtt ctttaatagt ggactcttgt tccaaactgg    420
aacaacactc aaccctatct cggtctattc ttttgattta taagggattt tgccgatttc    480
ggcctattgg ttaaaaaatg agctgattta acaaaaattt aacgcgaatt ttaacaaaat    540
attaacgttt acaatttcag gtggcacttt tcggggaaat gtgcgcggaa cccctatttg    600
tttatttttc taaatacatt caaatatgta tccgctcatg agacaataac cctgataaat    660
gcttcaataa tattgaaaaa ggaagagtat gagtattcaa catttccgtg tcgcccttat    720
tccctttttt gcggcatttt gccttcctgt ttttgctcac ccagaaacgc tggtgaaagt    780
aaaagatgct gaagatcagt tgggtgcacg agtgggttac atcgaactgg atctcaacag    840
cggtaagatc cttgagagtt ttcgccccga agaacgtttt ccaatgatga gcacttttaa    900
agttctgcta tgtggcgcgg tattatcccg tattgacgcc gggcaagagc aactcggtcg    960
ccgcatacac tattctcaga atgacttggt tgagtactca ccagtcacag aaaagcatct   1020
tacggatggc atgacagtaa gagaattatg cagtgctgcc ataaccatga gtgataacac   1080
tgcggccaac ttacttctga caacgatcgg aggaccgaag gagctaaccg cttttttgca   1140
caacatgggg gatcatgtaa ctcgccttga tcgttgggaa ccggagctga atgaagccat   1200
accaaacgac gagcgtgaca ccacgatgcc tgtagcaatg gcaacaacgt tgcgcaaact   1260
attaactggc gaactactta ctctagcttc ccggcaacaa ttaatagact ggatggaggc   1320
ggataaagtt gcaggaccac ttctgcgctc ggcccttccg gctggctggt ttattgctga   1380
taaatctgga gccggtgagc gtgggtctcg cggtatcatt gcagcactgg ggccagatgg   1440
taagccctcc cgtatcgtag ttatctacac gacggggagt caggcaacta tggatgaacg   1500
aaatagacag atcgctgaga taggtgcctc actgattaag cattggtaac tgtcagacca   1560
agtttactca tatatacttt agattgattt aaaacttcat ttttaattta aaaggatcta   1620
ggtgaagatc ctttttgata atctcatgac caaaatccct taacgtgagt tttcgttcca   1680
cgtaatctgc tgcttgcaaa caaaaaaacc accgctacca gcggtggttt gtttgccgga   1740
tcaagagcta ccaactcttt ttccgaaggt aactggcttc agcagagcgc agataccaaa   1800
tactgtcctt ctagtgtagc cgtagttagg ccaccacttc aagaactctg tagcaccgcc   1860
tacatacctc gctctgctaa tcctgttacc agtggctgct gccagtggcg ataagtcgtg   1920
tcttaccggg ttggactcaa gacgatagtt accggataag gcgcagcggt cgggctgaac   1980
ggggggttcg tgcacacagc ccagcttgga gcgaacgacc tacaccgaac tgagatacct   2040
acagcgtgag cattgagaaa gcgccacgct tcccgaaggg agaaaggcgg acaggtatcc   2100
ggtaagcggc agggtcggaa caggagagcg cacgagggag cttccagggg gaaacgcctg   2160
gtatctttat agtcctgtcg ggtttcgcca cctctgactt gagcgtcgat ttttgtgatg   2220
ctcgtcaggg gggcggagcc tatggaaaaa cgccagcaac gcggcctttt tacggttcct   2280
ggccttttgc tggccttttg ctcacatgtt ctttcctgcg ttatcccctg attctgtgga   2340
taaccgtatt accgcctttg agtgagctga taccgctcgc cgcagccgaa cgaccgagcg   2400
```

-continued

```
cagcgagtca gtgagcgagg aagcggaaga gcgcctgatg cggtattttc tccttacgca   2460
tctgtgcggt atttcacacc gcagaccagc cgcgtaacct ggcaaaatcg gttacggttg   2520
agtaataaat ggatgccctg cgtaagcggg tgtgggcgga caataaagtc ttaaactgaa   2580
caaaatagat ctaaactatg acaataaagt cttaaactag acagaatagt tgtaaactga   2640
aatcagtcca gttatgctgt gaaaaagcat actggacttt tgttatggct aaagcaaact   2700
cttcattttc tgaagtgcaa attgcccgtc gtattaaaga ggggcgtggc caagggcatg   2760
gtaaagacta tattcgcggc gttgtgacaa tttaccgaac aactccgcgg ccgggaagcc   2820
gatctcggct tgaacgaatt gttaggtggc ggtacttggg tcgatatcaa agtgcatcac   2880
ttcttcccgt atgcccaact ttgtatagag agccactgcg ggatcgtcac cgtaatctgc   2940
ttgcacgtag atcacataag caccaagcgc gttggcctca tgcttgagga gattgatgag   3000
cgcggtggca atgccctgcc tccggtgctc gccggagact gcgagatcat agatatagat   3060
ctcactacgc ggctgctcaa acctgggcag aacgtaagcc gcgagagcgc caacaaccgc   3120
ttcttggtcg aaggcagcaa gcgcgatgaa tgtcttacta cggagcaagt tcccgaggta   3180
atcggagtcc ggctgatgtt gggagtaggt ggctacgtct ccgaactcac gaccgaaaag   3240
atcaagagca gcccgcatgg atttgacttg gtcagggccg agcctacatg tgcgaatgat   3300
gcccatactt gagccaccta actttgtttt agggcgactg ccctgctgcg taacatcgtt   3360
cttgctgctt ggatgcccga ggcatagact gtacaaaaaa acagtcataa caagccatga   3420
aaaccgccac tgcgccgtta ccaccgctgc gttcggtcaa ggttctggac cagttgcgtg   3480
agcgcatacg ctacttgcat tacagtttac gaaccgaaca ggcttatgtc aactgggttc   3540
gtgccttcat ccgtttccac ggtgtgcgtc acccggcaac cttgggcagc agcgaagtcg   3600
aggcatttct gtcctggctg gcgaacgagc gcaaggtttc ggtctccacg catcgtcagg   3660
cattggcggc cttgctgttc ttctacggca aggtgctgtg cacggatctg ccctggcttc   3720
aggagatcgg tagacctcgg ccgtcgcggc gcttgccggt ggtgctgacc ccggatgaag   3780
tggttcgcat cctcggtttt ctggaaggcg agcatcgttt gttcgcccag gactctagct   3840
atagttctag tggttggcct acagctttgt ttaaacaaag ctgtacccgt agtggctatg   3900
gcagggcttg ccgccccgac gttggctgcg agccctgggc cttcacccga acttgggggt   3960
tggggtgggg aaaaggaaga aacgcgggcg tattggtccc aatggggtct cggtggggta   4020
tcgacagagt gccagccctg ggaccgaacc ccgcgtttat gaacaaacga cccaacaccc   4080
gtgcgtttta ttctgtcttt ttattgccgt catagcgcgg gttccttccg gtattgtctc   4140
cttccgtgtt tcagttagcc tcccccatct cccggtaccg catgctatgc atcagctgct   4200
agcaccatgg ctcgagatcc cgggtgatca agtcttcgtc gagtgattgt aaataaaatg   4260
taatttacag tatagtattt taattaatat acaaatgatt tgataataat tcttatttaa   4320
ctataatata ttgtgttggg ttgaattaaa ggtccgtata ctagtatcga ttcgcgacct   4380
actccggaat attaatagat catggagata attaaaatga taaccatctc gcaaataaat   4440
aagtatttta ctgttttcgt aacagttttg taataaaaaa acctataaat attccggatt   4500
attcataccg tcccaccatc gggcgcggat cctcgagatg ggtaaccatg acaagcgacg   4560
atggaaaaag aatttcatag ccgtctcagc agccaaccgc tttaagaaaa tctcatcctc   4620
cggggcagct agctggagcc acccgcagtt cgaaaaaggc gccgacgacg acgacgacaa   4680
gggctcccat atgtctggga ttgtaccgca gctgcaaaat attgtatcca cagtgaatct   4740
tggttgtaaa cttgacctaa agaccattgc acttcgtgcc cgaaacgccg aatataatcc   4800
```

-continued

```
caagcggttt gctgcggtaa tcatgaggat aagagagcca cgaaccacgg cactgatttt   4860

cagttctggg aaaatggtgt gcacaggagc caagagtgaa gaacagtcca gactggcagc   4920

aagaaaatat gctagagttg tacagaagtt gggttttcca gctaagttct tggacttcaa   4980

gattcagaac atggtgggga gctgtgatgt gaagtttcct ataaggttag aaggccttgt   5040

gctcacccac caacaattta gtagttatga gccagagtta tttcctggtt taatctacag   5100

aatgatcaaa cccagaattg ttctccttat tttgtttct ggaaaagttg tattaacagg   5160

tgctaaagtc agagcagaaa tttatgaagc atttgaaaac atctacccta ttctaaaggg   5220

attcaggaag acgacgcggt ccggaggtaa cggatccgaa aacctgtatt ttcagggttc   5280

tgggattgta ccgcagctgc aaaatattgt atccacagtg aatcttggtt gtaaacttga   5340

cctaaagacc attgcacttc gtgcccgaaa cgccgaatat aatcccaagc ggtttgctgc   5400

ggtaatcatg aggataagag agccacgaac cacggcactg attttcagtt ctgggaaaat   5460

ggtgtgcaca ggagccaaga gtgaagaaca gtccagactg gcagcaagaa aatatgctag   5520

agttgtacag aagttgggtt ttccagctaa gttcttggac ttcaagattc agaacatggt   5580

ggggagctgt gatgtgaagt ttcctataag gttagaaggc cttgtgctca cccaccaaca   5640

atttagtagt tatgagccag agttatttcc tggtttaatc tacagaatga tcaaacccag   5700

aattgttctc cttatttttg tttctggaaa agttgtatta acaggtgcta aagtcagagc   5760

agaaatttat gaagcatttg aaaacatcta ccctattcta aagggattca ggaagacgac   5820

gcggtccgga ggtaacggat ccgaaaacct gtattttcag ggttctggga ttgtaccgca   5880

gctgcaaaat attgtatcca cagtgaatct tggttgtaaa cttgacctaa agaccattgc   5940

acttcgtgcc cgaaacgccg aatataatcc caagcggttt gctgcggtaa tcatgaggat   6000

aagagagcca cgaaccacgg cactgatttt cagttctggg aaaatggtgt gcacaggagc   6060

caagagtgaa gaacagtcca gactggcagc aagaaaatat gctagagttg tacagaagtt   6120

gggttttcca gctaagttct tggacttcaa gattcagaac atggtgggga gctgtgatgt   6180

gaagtttcct ataaggttag aaggccttgt gctcacccac caacaattta gtagttatga   6240

gccagagtta tttcctggtt taatctacag aatgatcaaa cccagaattg ttctccttat   6300

tttgtttct ggaaaagttg tattaacagg tgctaaagtc agagcagaaa tttatgaagc   6360

atttgaaaac atctacccta ttctaaaggg attcaggaag acgacgcggt ccggccacca   6420

tcatcaccac cattgataag ctagcggccg ctttcgaatc tagagcctgc agtctcgaca   6480

agcttgtcga gaagtactag aggatcataa tcagccatac cacatttgta gaggttttac   6540

ttgctttaaa aaacctccca cacctccccc tgaacctgaa acataaaatg aatgcaattg   6600

ttgttgttaa cttgtttatt gcagcttata atggttacaa ataaagcaat agcatcacaa   6660

atttcacaaa taaagcattt ttttcactgc attctagttg tggtttgtcc aaactcatca   6720

atgtatctta tcatgtctgg atctgatcac tgcttgagcc taggagatcc gaaccagata   6780

agtgaaatct agttccaaac tattttgtca tttttaattt tcgtattagc ttacgacgct   6840

acacccagtt cccatctatt ttgtcactct tccctaaata atccttaaaa actccatttc   6900

cacccctccc agttcccaac gccaactcca tgtgacaaac cgtcatcttc ggctacttt    6959
```

<210> SEQ ID NO 4
<211> LENGTH: 12950
<212> TYPE: DNA
<213> ORGANISM: Artificial Sequence
<220> FEATURE:

<223> OTHER INFORMATION: Synthetic Construct; Plasmid pUCDMSTAF1TBPcTAF2

<400> SEQUENCE: 4

```
aattctgtca gccgttaagt gttcctgtgt cactgaaaat tgctttgaga ggctctaagg     60
gcttctcagt gcgttacatc cctggcttgt tgtccacaac cgttaaacct taaaagcttt    120
aaaagcctta tatattcttt tttttcttat aaaacttaaa accttagagg ctatttaagt    180
tgctgattta tattaatttt attgttcaaa catgagagct tagtacgtga aacatgagag    240
cttagtacgt tagccatgag agcttagtac gttagccatg agggtttagt tcgttaaaca    300
tgagagctta gtacgttaaa catgagagct tagtacgtga aacatgagag cttagtacgt    360
actatcaaca ggttgaactg ctgatcaaca gatcctctac gcggccgcgg taccataact    420
tcgtatagca tacattatac gaagttatct ggagtacccg tagtggctat ggcagggctt    480
gccgccccga cgttggctgc gagccctggg ccttcacccg aacttggggg ttggggtggg    540
gaaaaggaag aaacgcgggc gtattggtcc caatggggtc tcggtggggt atcgacagag    600
tgccagccct gggaccgaac cccgcgttta tgaacaaacg acccaacacc cgtgcgtttt    660
attctgtctt tttattgccg tcatagcgcg ggttccttcc ggtattgtct ccttccgtgt    720
ttcagttagc ctcccccatc tcccggtacc gcatgctatg catcagctgc tagcaccatg    780
gctcgagatc ccgggtgatc aagtcttcgt cgagtgattg taaataaaat gtaatttaca    840
gtatagtatt ttaattaata tacaaatgat ttgataataa ttcttattta actataatat    900
attgtgttgg gttgaattaa aggtccgtat actagtatcg attcgcgacc tactccggaa    960
tattaataga tcatggagat aattaaaatg ataaccatct cgcaaataaa taagtatttt   1020
actgttttcg taacagtttt gtaataaaaa aacctataaa tattccggat tattcatacc   1080
gtcccaccat cgggcgcgga tcctcgagat gggtaaccat gacaagcgac gatggaaaaa   1140
gaatttcata gccgtctcag cagccaaccg ctttaagaaa atctcatcct ccggggcagc   1200
tagctggagc cacccgcagt tcgaaaaagg cgccgacgac gacgacgaca agggctccca   1260
tatgggaccc ggctgcgatt tgctgctgcg gacagcagct accatcactg ctgccgccat   1320
catgtcagac acggacagcg acgaagattc cgctggaggc ggcccatttt ctttagcggg   1380
tttccttttc ggcaacatca atggagccgg gcagctggag ggggaaagcg tcttggatga   1440
tgaatgtaag aagcacttgg caggcttggg ggctttgggg ctgggcagcc tgatcactga   1500
actcacggca aatgaagaat tgaccgggac tgacggtgcc ttggtaaatg atgaagggtg   1560
ggttaggagt acagaagatg ctgtggacta ttcagacatc aatgaggtgg cagaagatga   1620
aagccgaaga taccagcaga cgatggggag cttgcagccc ctttgccact cagattatga   1680
tgaagatgac tatgatgctg attgtgaaga cattgattgc aagttgatgc ctcctccacc   1740
tccacccccg ggaccaatga agaaggataa ggaccaggat tctattactg gtgagaaagt   1800
ggacttcagt agttcctctg actcagaatc tgagatggga cctcaggaag caacacaggc   1860
agaatctgaa gatggaaagc tgacccttcc attggctggg attatgcagc atgatgccac   1920
caagctgttg ccaagtgtca cagaactttt tccagaattt cgacctggaa aggtgttacg   1980
ttttctacgt ctttttggac cagggaagaa tgtcccatct gtttggcgga gtgctcggag   2040
aaagaggaag aagaagcacc gtgagctgat acaggaagag cagatccagg aggtggagtg   2100
ctcagtagaa tcagaagtca gccagaagtc tttgtggaac tacgactacg ctccaccacc   2160
acctccagag cagtgtctct ctgatgatga aatcacgatg atggctcctg tggagtccaa   2220
attttcccaa tcaactggag atatagataa agtgacagat accaaaccaa gagtggctga   2280
```

```
gtggcgttat gggcctgccc gactgtggta tgatatgctg ggtgtccctg aagatggcag   2340
tgggtttgac tatggcttca aactgagaaa gacagaacat gaacctgtga taaaatctag   2400
aatgatagag gaatttagga aacttgagga aaacaatggc actgatcttc tggctgatga   2460
aaacttcctg atggtgacac agctgcattg ggaggatgat atcatctggg atggggagga   2520
tgtcaaacac aaagggacaa aacctcagcg tgcaagcctg gcaggctggc ttccttctag   2580
catgactagg aatgcgatgg cttacaatgt tcagcaaggt tttgcagcca ctcttgatga   2640
tgacaaacct tggtactcca tttttcccat tgacaatgag gatctggtat atggacgctg   2700
ggaggacaat atcatttggg atgctcaggc catgccccgg ctgttggaac ctcctgtttt   2760
gacacttgat cccaatgatg agaacctcat tttggaaatt cctgatgaga aggaagaggc   2820
cacctctaac tccccctcca aggagagtaa gaaggaatca tctctgaaga agagtcgaat   2880
tctcttaggg aaaacaggag tcatcaagga ggaaccacag cagaacatgt ctcagccaga   2940
agtgaaagat ccatggaatc tctccaatga tgagtattat tatcccaagc aacagggtct   3000
tcgaggcacc tttggaggga atattatcca gcattcaatt cctgctgtgg aattacggca   3060
gcccttcttt cccacccaca tggggcccat caaactccgg cagttccatc gcccacctct   3120
gaaaaagtac tcatttggtg cactttctca gccaggtccc cactcagtcc aacctttgct   3180
aaagcacatc aaaaaaaagg ccaagatgag agaacaagag aggcaagctt caggtggtgg   3240
agagatgttt tttatgcgca cacctcagga cctcacaggc aaagatggtg atcttattct   3300
tgcagaatat agtgaggaaa atggaccctt aatgatgcag gttggcatgg caaccaagat   3360
aaagaactat tataaacgga aacctggaaa agatcctgga gcaccagatt gtaaatatgg   3420
ggaaactgtt tactgccata catctccttt cctgggttct ctccatcctg gccaattgct   3480
gcaagcattt gagaacaacc tttttcgtgc tccaatttat cttcataaga tgccagaaac   3540
tgatttcttg atcattcgga caagacaggg ttactatatt cgggaattag tggatatttt   3600
tgtggttggc cagcagtgtc ccttgtttga agttcctggg cctaactcca aaagggccaa   3660
tacgcatatt cgagactttc tacaggtttt tatttaccgc cttttctgga aaagtaaaga   3720
tcggccacgg aggatacgaa tggaagatat aaaaaaagcc tttccttccc attcagaaag   3780
cagcatccgg aagaggctaa agctctgcgc tgacttcaaa cgcacaggga tggactcaaa   3840
ctggtgggtg cttaagtctg attttcgttt accaacggaa gaagagatca gagctatggt   3900
gtcaccagag cagtgctgtg cttattatag catgatagct gcagagcaac gactgaagga   3960
tgctggctat ggtgagaaat cctttttgc tccagaagaa gaaaatgagg aagatttcca   4020
gatgaagatt gatgatgaag ttcgcactgc cccttggaac accacaaggg ccttcattgc   4080
tgccatgaag ggcaagtgtc tgctagaggt gactggggtg gcagatccca cggggtgtgg   4140
tgaaggattc tcctatgtga agattccaaa caaaccaaca cagcagaagg atgataaaga   4200
accgcagcca gtgaagaaga cagtgacagg aacagatgca gaccttcgtc gcctttccct   4260
gaaaaatgcc aagcaacttc tacgtaaatt tggtgtgcct gaggaagaga ttaaaaagtt   4320
gtcccgctgg gaagtgattg atgtggtgcg cacaatgtca acagaacagg ctcgttctgg   4380
agaggggccc atgagtaaat ttgcccgtgg atcaaggttt tctgtggctg agcatcaaga   4440
gcgttacaaa gaggaatgtc agcgcatctt tgacctacag aacaaggttc tgtcatcaac   4500
tgaagtctta tcaactgaca cagacagcag ctcagctgaa gatagtgact ttgaagaaat   4560
gggaaagaac attgagaaca tgttgcagaa caagaaaacc agctctcagc tttcacgtga   4620
```

```
acgggaggaa caggagcgga aggaactaca gcgaatgcta ctggcagcag gctcagcagc   4680
atccggaaac aatcacagag atgatgacac agcttccgtg actagcctta actcttctgc   4740
cactggacgc tgtctcaaga tttatcgcac gtttcgagat gaagagggga aagagtatgt   4800
tcgctgtgag acagtccgaa aaccagctgt cattgatgcc tatgtgcgca tacggactac   4860
aaaagatgag gaattcattc gaaaatttgc cctttttgat gaacaacatc gggaagagat   4920
gcgaaaagaa cggcggagga ttcaagagca actgaggcgg cttaagagga accaggaaaa   4980
ggagaagctt aagggtcctc ctgagaagaa gcccaagaaa atgaaggagc gtcctgacct   5040
aaaactgaaa tgtggggcat gtggtgccat tggacacatg aggactaaca aattctgccc   5100
cctctattat caaacaaatg cgccaccttc caaccctgtt gccatgacag aagaacagga   5160
ggaggagttg gaaaagacag tcattcataa tgataatgaa gaacttatca aggttgaagg   5220
gaccaaaatt gtcttgggga aacagctaat tgagagtgcg gatgaggttc gcagaaaatc   5280
tctggttctc aagtttccta aacagcagct tcctccaaag aagaaacggc gagttggaac   5340
cactgttcac tgtgactatt tgaatagacc tcataagtcc atccaccggc gccgcacaga   5400
ccctatggtg acgctgtcgt ccatcttgga gtctatcatc aatgacatga gagatcttcc   5460
aaatacatac cctttccaca ctccagtcaa tgcaaaggtt gtaaaggact actacaaaat   5520
catcactcgg ccaatggacc tacaaacact ccgcgaaaac gtgcgtaaac gcctctaccc   5580
atctcgggaa gagttcagag agcatctgga gctaattgtg aaaaatagtg caacctacaa   5640
tgggccaaaa cactcattga ctcagatctc tcaatccatg ctggatctct gtgatgaaaa   5700
actcaaagag aaagaagaca aattagctcg cttagagaaa gctatcaacc ccttgctgga   5760
tgatgatgac caagtggcgt tttctttcat tctggacaac attgtcaccc agaaaatgat   5820
ggcagttcca gattcttggc catttcatca cccagttaat aagaaatttg ttccagatta   5880
ttacaaagtg attgtcaatc caatggattt agagaccata cgtaagaaca tctccaagca   5940
caagtatcag agtcgggaga gctttctgga tgatgtaaac cttattctgg ccaacagtgt   6000
taagtataat ggacctgaga gtcagtatac taagactgcc caggagattg tgaacgtctg   6060
ttaccagaca ttgactgagt atgatgaaca tttgactcaa cttgagaagg atatttgtac   6120
tgctaaagaa gcagctttgg aggaagcaga attagaaagc ctggacccaa tgaccccagg   6180
gccctacacg cctcagcctc ctgatttgta tgataccaac acatccctca gtatgtctcg   6240
agatgcctct gtatttcaag atgagagcaa tatgtctgtc ttggatattc ccagtgccac   6300
tccagaaaag caggtaacac aggaaggtga agatggagat ggtgatcttg cagatgaaga   6360
ggaaggaact gtacaacagc ctcaagccag tgtcctgtat gaggatttgc ttatgtctga   6420
aggagaagat gatgaggaag atgctgggag tgatgaagaa ggagacaatc ctttctctgc   6480
tatccagctg agtgaaagtg gaagtgactc tgatgtggga tctggtggaa taagacccaa   6540
acaaccccgc atgcttcagg agaacacaag gatggacatg gaaaatgaag aaagcatgat   6600
gtcctatgag ggagacggtg gggaggcttc ccatggtttg gaggatagca acatcagtta   6660
tgggagctat gaggagcctg atcccaagtc gaacacccaa gacacaagct tcagcagcat   6720
cggtgggtat gaggtatcag aggaggaaga agatgaggag gaggaagagc agcgctctgg   6780
gccgagcgta ctaagccagg tccacctgtc agaggacgag gaggacagtg aggatttcca   6840
ctccattgct ggggacagtg acttggactc tgatgaacgg tccggaggta acggatccga   6900
aaacctgtat tttcagggtt ctgggattgt accgcagctg caaaatattg tatccacagt   6960
gaatcttggt tgtaaacttg acctaaagac cattgcactt cgtgcccgaa acgccgaata   7020
```

```
taatcccaag cggtttgctg cggtaatcat gaggataaga gagccacgaa ccacggcact   7080

gattttcagt tctgggaaaa tggtgtgcac aggagccaag agtgaagaac agtccagact   7140

ggcagcaaga aaatatgcta gagttgtaca gaagttgggt tttccagcta agttcttgga   7200

cttcaagatt cagaacatgg tggggagctg tgatgtgaag tttcctataa ggttagaagg   7260

ccttgtgctc acccaccaac aatttagtag ttatgagcca gagttatttc ctggtttaat   7320

ctacagaatg atcaaaccca gaattgttct ccttattttt gtttctggaa aagttgtatt   7380

aacaggtgct aaagtcagag cagaaattta tgaagcattt gaaaacatct accctattct   7440

aaagggattc aggaagacga cgcggtccgg aggtaacgga tccgaaaacc tgtattttca   7500

gggtgactac aaagacgatg acgataaaaa caggaagaaa ggagacaagg gctttgaaag   7560

cccaaggcca tataaattaa cccatcaggt cgtctgcatc aacaacataa atttccagag   7620

aaaatctgtt gtgggatttg tggaactgac tatatttccc acagttgcaa acttgaatag   7680

aatcaagttg aacagcaaac agtgtagaat ataccgagta aggatcaatg atttagaggc   7740

tgcttttatt tataatgacc caaccttgga agtttgtcac agtgaatcaa aacagagaaa   7800

cctcaattat ttttccaatg cttatgcagc tgcagttagt gctgtggacc ctgatgcagg   7860

aaatggagaa ctttgcatta aggttccatc agagctatgg aaacacgttg atgagttaaa   7920

ggtcctgaag atacacatca atttttcttt ggatcagccc aaaggaggtc ttcattttgt   7980

ggtacccagt gtagagggaa gtatggcaga gagaggtgct catgttttct cttgtgggta   8040

tcaaaattct acaagatttt ggttcccttg tgttgattca tactctgaat tgtgtacatg   8100

gaaattagaa tttacagtag atgctgcaat ggttgctgtt tctaatggcg atttggtgga   8160

gacagtgtat actcatgata tgaggaagaa aactttccat tatatgctta ccattcctac   8220

agcagcgtca aatatctcct tggccattgg accatttgaa atactggtag atccatacat   8280

gcatgaggtt actcattttt gtttgcccca acttcttcca ttgctgaaac ataccacatc   8340

ataccttcat gaagtctttg aattttatga agaaattctt acatgtcgtt acccatactc   8400

ctgttttaag actgtcttca ttgatgaggc ttatgttgaa gtggctgctt atgcttccat   8460

gagcattttt agcacaaatc ttttacacag tgccatgatt atagatgaga cacctttgac   8520

tagaaggtgt ttagcccaat ccttggccca gcagtttttt ggttgtttca tatctagaat   8580

gtcttggtct gatgaatggg tgctgaaggg aatttcaggc tatatctatg gactttggat   8640

gaaaaaaact tttggtgtta atgagtaccg ccattggatt aaagaggagc tagacaaaat   8700

agtggcatat gaactaaaaa ctggtggggt tttactacat cccatatttg gtggaggaaa   8760

agagaaggat aatccggctt cccatctaca cttttcaata aagcatccac atacactgtc   8820

ctgggaatac tacactatgt ttcagtgtaa agcccacctt gtgatgagat tgattgaaaa   8880

taggatcagt atggaattta tgctacaagt tttcaataaa ctgctaagtc tggctagtac   8940

tgcttcatct cagaagttcc agtcacatat gtggagtcag atgttggttt ccacatctgg   9000

gtttttgaaa tccatttcaa atgtctctgg caaagatatt cagccgttaa taaagcagtg   9060

ggtagatcag agtggagtgg taaaatttta tggaagtttt gcatttaata gaaaacgaaa   9120

tgtcttggaa ctggaaataa aacaggacta tacatctcct ggaactcaga aatacgtggg   9180

accacttaaa gtgacagtgc aggagttaga tggatccttc aatcatacac tgcaaattga   9240

agaaaacagc cttaaacatg atataccctg ccattccaaa agtagaagga ataaaaagaa   9300

aaaaatccca ctgatgaatg gagaagaagt tgacatggat ctttctgcaa tggatgctga   9360
```

-continued

```
ttccccttg ctgtggataa ggatagaccc agatatgtca gtattgagga aggtagaatt   9420
tgagcaagct gattttatgt ggcagtatca gctccgctat gagagagatg ttgttgcaca   9480
gcaggaatcc attttggctt tggaaaaatt ccctactcca gcatctcggc ttgcactcac   9540
tgatatatta gaacaagagc agtgtttcta cagagtaaga atgtcagctt gcttctgtct   9600
tgcaaagatt gcaaattcca tggtgagcac atggacagga ccaccagcca tgaagtcact   9660
cttcactagg atgttttgtt gtaaaagttg tccaaacatt gtgaaaacaa acaactttat   9720
gagctttcaa agttattttc tacagaagac tatgccagtt gcaatggctt tattaagaga   9780
tgttcataat ctttgtccta aagaagtctt aacgtttatt ttagacttaa tcaagtacaa   9840
tgacaacagg aaaaataagt tttcagataa ctattatcgt gcagaaatga ttgatgccct   9900
ggccaactct gttacacctg cagtcagtgt gaataatgaa gttagaactt tggataactt   9960
aaatcctgat gtgcgactca ttcttgaaga aatcaccaga tttttgaata tggaaaaact  10020
tcttccgagt tacaggcata ccatcactgt cagttgtttg agagccatac gggtacttca  10080
gaagaacgga catgtgccaa gtgatccagc tctttttaaa tcttatgctg aatatggcca  10140
ctttgtggac attaggatag cagctttgga agcagttgtt gattatacta aagtggacag  10200
aagttatgaa gaactgcaat ggctacttaa tatgattcag aatgaccctg taccctatgt  10260
aaggcataag attctcaaca tgttgactaa gaacccacca tttactaaga acatggagtc  10320
tcccttatgc aatgaagccc tggtagatca actttggaaa cttatgaatt ctggtacttc  10380
acatgactgg aggttacggt gtggtgctgt ggacttgtac ttcacacttt ttggcctcag  10440
tagaccttcc tgtttaccct tgccagagct tgggttggtt cttaatctaa aggagaaaaa  10500
agctgtcttg aatcctacca taattccaga gtcagtagca ggcaaccaag aagctgcaaa  10560
taatccaagc agtcacccac agctagttgg atttcagaac cctttttcca gttctcaaga  10620
tgaggaggag attgatatgg atactgttca tgatagccag gccttcattt cccatcattt  10680
aaacatgctt gaaaggccgt caactccagg gctctcgaag tatcggccag ctagctcccg  10740
atctgcttta ataccccagc actcagcagg ctgcgacagc acacccacca caaaaccccca  10800
gtggagtttg gaacttgcac ggaagggaac aggtaaagaa caagcacctt tggagatgag  10860
tatgcatccg gcggcaagcg ctccactctc agtctttact aaggaatcta cagcctccaa  10920
acacagtgac caccatcacc accatcacca tgagcacaag aaaaagaaga agaagcataa  10980
acataagcac aaacacaagc ataagcatga cagtaaagaa aaggacaagg agcctttcac  11040
tttctccagc cctgccagtg gcaggtctat tcgttctcct tccctttcag accggtccgg  11100
ccaccatcat caccaccatt gataagctag cggccgcttt cgaatctaga gcctgcagtc  11160
tcgacaagct tgtcgagaag tactagagga tcataatcag ccataccaca tttgtagagg  11220
ttttacttgc tttaaaaaac ctcccacacc tcccccctgaa cctgaaacat aaaatgaatg  11280
caattgttgt tgttaacttg tttattgcag cttataatgg ttacaaataa agcaatagca  11340
tcacaaattt cacaaataaa gcattttttt cactgcattc tagttgtggt ttgtccaaac  11400
tcatcaatgt atcttatcat gtctggatct gatcactgct tgagcctaga agatccggct  11460
gctaacaaag cccgaaagga agctgagttg gctgctgcca ccgctgagca ataactagca  11520
taaccccttg gggcctctaa acgggtcttg aggggttttt tgctgaaagg aggaactata  11580
tccggatctg aacaggaggg acagctgata gaaacagaag ccactggagc acctcaaaaa  11640
caccatcata cactaaatca gtaagttggc agcatcaccc gacgcacttt gcgccgaata  11700
aatacctgtg acggaagatc acttcgcaga ataaataaat cctggtgtcc ctgttgatac  11760
```

cgggaagccc tgggccaact tttggcgaaa atgagacgtt gatcggcacg taagaggttc 11820
caactttcac cataatgaaa taagatcact accgggcgta ttttttgagt tatcgagatt 11880
ttcaggagct aaggaagcta aaatggagaa aaaaatcact ggatatacca ccgttgatat 11940
atcccaatgg catcgtaaag aacattttga ggcatttcag tcagttgctc aatgtaccta 12000
taaccagacc gttcagctgg atattacggc ctttttaaag accgtaaaga aaaataagca 12060
caagttttat ccggccttta ttcacattct tgcccgcctg atgaatgctc atccggaatt 12120
ccgtatggca atgaaagacg gtgagctggt gatatgggat agtgttcacc cttgttacac 12180
cgttttccat gagcaaactg aaacgttttc atcgctctgg agtgaatacc acgacgattt 12240
ccggcagttt ctacacatat attcgcaaga tgtggcgtgt tacggtgaaa acctggccta 12300
tttccctaaa gggtttattg agaatatgtt tttcgtctca gccaatccct gggtgagttt 12360
caccagtttt gatttaaacg tggccaatat ggacaacttc ttcgcccccg ttttcaccat 12420
gggcaaatat tatacgcaag gcgacaaggt gctgatgccg ctggcgattc aggttcatca 12480
tgccgtctgt gatggcttcc atgtcggcag aatgcttaat gaattacaac agtactgcga 12540
tgagtggcag ggcggggcgt aattttttta aggcagttat tggtgccctt aaacgcctgg 12600
tgctacgcct gaataagtga taataagcgg atgaatggca gaaattcgaa agcaaattcg 12660
acccggtcgt cggttcaggg cagggtcgtt aaatagccgc ttatgtctat tgctggttta 12720
ccggtttatt gactaccgga agcagtgtga ccgtgtgctt ctcaaatgcc tgaggccagt 12780
ttgctcaggc tctccccgtg gaggtaataa ttgacgatat gatcatttat tctgcctccc 12840
agagcctgac attcatccgg ggtcagcacc gtttctgcgg actggctttc tacgtgttcc 12900
gcttccttta gcagcccttg cgccctgagt gcttgcggca gcgtgaagct 12950

<210> SEQ ID NO 5
<211> LENGTH: 8735
<212> TYPE: DNA
<213> ORGANISM: Artificial Sequence
<220> FEATURE:
<223> OTHER INFORMATION: Synthetic Construct; Plasmid pFBDO[HisTEVTAF6TAF9]his

<400> SEQUENCE: 5
ttctctgtca cagaatgaaa atttttctgt catctcttcg ttattaatgt ttgtaattga 60
ctgaatatca acgcttattt gcagcctgaa tggcgaatgg gacgcgccct gtagcggcgc 120
attaagcgcg gcgggtgtgg tggttacgcg cagcgtgacc gctacacttg ccagcgccct 180
agcgcccgct cctttcgctt tcttcccttc ctttctcgcc acgttcgccg gctttccccg 240
tcaagctcta aatcgggggc tccctttagg gttccgattt agtgctttac ggcacctcga 300
ccccaaaaaa cttgattagg gtgatggttc acgtagtggg ccatcgccct gatagacggt 360
ttttcgccct ttgacgttgg agtccacgtt ctttaatagt ggactcttgt tccaaactgg 420
aacaacactc aaccctatct cggtctattc ttttgattta taagggattt tgccgatttc 480
ggcctattgg ttaaaaaatg agctgattta acaaaaattt aacgcgaatt ttaacaaaat 540
attaacgttt acaatttcag gtggcacttt tcggggaaat gtgcgcggaa cccctatttg 600
tttatttttc taaatacatt caaatatgta tccgctcatg agacaataac cctgataaat 660
gcttcaataa tattgaaaaa ggaagagtat gagtattcaa catttccgtg tcgcccttat 720
tccctttttt gcggcatttt gccttcctgt ttttgctcac ccagaaacgc tggtgaaagt 780
aaaagatgct gaagatcagt tgggtgcacg agtgggttac atcgaactgg atctcaacag 840

```
cggtaagatc cttgagagtt ttcgccccga agaacgtttt ccaatgatga gcacttttaa    900

agttctgcta tgtggcgcgg tattatcccg tattgacgcc gggcaagagc aactcggtcg    960

ccgcatacac tattctcaga atgacttggt tgagtactca ccagtcacag aaaagcatct   1020

tacggatggc atgacagtaa gagaattatg cagtgctgcc ataaccatga gtgataacac   1080

tgcggccaac ttacttctga caacgatcgg aggaccgaag gagctaaccg cttttttgca   1140

caacatgggg gatcatgtaa ctcgccttga tcgttgggaa ccggagctga atgaagccat   1200

accaaacgac gagcgtgaca ccacgatgcc tgtagcaatg gcaacaacgt tgcgcaaact   1260

attaactggc gaactactta ctctagcttc ccggcaacaa ttaatagact ggatggaggc   1320

ggataaagtt gcaggaccac ttctgcgctc ggcccttccg gctggctggt ttattgctga   1380

taaatctgga gccggtgagc gtgggtctcg cggtatcatt gcagcactgg ggccagatgg   1440

taagccctcc cgtatcgtag ttatctacac gacggggagt caggcaacta tggatgaacg   1500

aaatagacag atcgctgaga taggtgcctc actgattaag cattggtaac tgtcagacca   1560

agtttactca tatatacttt agattgattt aaaacttcat ttttaattta aaaggatcta   1620

ggtgaagatc ctttttgata atctcatgac caaaatccct taacgtgagt tttcgttcca   1680

cgtaatctgc tgcttgcaaa caaaaaaacc accgctacca gcggtggttt gtttgccgga   1740

tcaagagcta ccaactcttt ttccgaaggt aactggcttc agcagagcgc agataccaaa   1800

tactgtcctt ctagtgtagc cgtagttagg ccaccacttc aagaactctg tagcaccgcc   1860

tacatacctc gctctgctaa tcctgttacc agtggctgct gccagtggcg ataagtcgtg   1920

tcttaccggg ttggactcaa gacgatagtt accggataag gcgcagcggt cgggctgaac   1980

ggggggttcg tgcacacagc ccagcttgga gcgaacgacc tacaccgaac tgagatacct   2040

acagcgtgag cattgagaaa gcgccacgct tcccgaaggg agaaaggcgg acaggtatcc   2100

ggtaagcggc agggtcggaa caggagagcg cacgagggag cttccagggg gaaacgcctg   2160

gtatctttat agtcctgtcg ggtttcgcca cctctgactt gagcgtcgat ttttgtgatg   2220

ctcgtcaggg gggcggagcc tatggaaaaa cgccagcaac gcggcctttt tacggttcct   2280

ggccttttgc tggccttttg ctcacatgtt ctttcctgcg ttatcccctg attctgtgga   2340

taaccgtatt accgcctttg agtgagctga taccgctcgc cgcagccgaa cgaccgagcg   2400

cagcgagtca gtgagcgagg aagcggaaga gcgcctgatg cggtattttc tccttacgca   2460

tctgtgcggt atttcacacc gcagaccagc cgcgtaacct ggcaaaatcg gttacggttg   2520

agtaataaat ggatgccctg cgtaagcggg tgtgggcgga caataaagtc ttaaactgaa   2580

caaaatagat ctaaactatg acaataaagt cttaaactag acagaatagt tgtaaactga   2640

aatcagtcca gttatgctgt gaaaaagcat actggacttt tgttatggct aaagcaaact   2700

cttcattttc tgaagtgcaa attgcccgtc gtattaaaga ggggcgtggc caagggcatg   2760

gtaaagacta tattcgcggc gttgtgacaa tttaccgaac aactccgcgg ccgggaagcc   2820

gatctcggct tgaacgaatt gttaggtggc ggtacttggg tcgatatcaa agtgcatcac   2880

ttcttcccgt atgcccaact ttgtatagag agccactgcg ggatcgtcac cgtaatctgc   2940

ttgcacgtag atcacataag caccaagcgc gttggcctca tgcttgagga gattgatgag   3000

cgcggtggca atgccctgcc tccggtgctc gccggagact gcgagatcat agatatagat   3060

ctcactacgc ggctgctcaa acctgggcag aacgtaagcc gcgagagcgc caacaaccgc   3120

ttcttggtcg aaggcagcaa gcgcgatgaa tgtcttacta cggagcaagt tcccgaggta   3180
```

```
atcggagtcc ggctgatgtt gggagtaggt ggctacgtct ccgaactcac gaccgaaaag   3240
atcaagagca gcccgcatgg atttgacttg gtcagggccg agcctacatg tgcgaatgat   3300
gcccatactt gagccaccta actttgtttt agggcgactg ccctgctgcg taacatcgtt   3360
cttgctgctt ggatgcccga ggcatagact gtacaaaaaa acagtcataa caagccatga   3420
aaaccgccac tgcgccgtta ccaccgctgc gttcggtcaa ggttctggac cagttgcgtg   3480
agcgcatacg ctacttgcat tacagtttac gaaccgaaca ggcttatgtc aactgggttc   3540
gtgccttcat ccgtttccac ggtgtgcgtc acccggcaac cttgggcagc agcgaagtcg   3600
aggcatttct gtcctggctg gcgaacgagc gcaaggtttc ggtctccacg catcgtcagg   3660
cattggcggc cttgctgttc ttctacggca aggtgctgtg cacggatctg ccctggcttc   3720
aggagatcgg tagacctcgg ccgtcgcggc gcttgccggt ggtgctgacc ccggatgaag   3780
tggttcgcat cctcggtttt ctggaaggcg agcatcgttt gttcgcccag gactctagct   3840
atagttctag tggttggcct acagctttgt ttaaacaaag ctgtacccgt agtggctatg   3900
gcagggcttg ccgccccgac gttggctgcg agccctgggc cttcacccga acttgggggt   3960
tggggtgggg aaaaggaaga aacgcgggcg tattggtccc aatggggtct cggtggggta   4020
tcgacagagt gccagccctg ggaccgaacc ccgcgtttat gaacaaacga cccaacaccc   4080
gtgcgtttta ttctgtcttt ttattgccgt catagcgcgg gttccttccg gtattgtctc   4140
cttccgtgtt tcagttagcc tcccccatct cccggtaccg catgctatgc atcagctgct   4200
agcaccatgg ctcgagatcc cgggtgatca agtcttcgtc gagtgattgt aaataaaatg   4260
taatttacag tatagtattt taattaatat acaaatgatt tgataataat tcttatttaa   4320
ctataatata ttgtgttggg ttgaattaaa ggtccgtata ctagtatcga ttcgcgacct   4380
actccggaat attaatagat catggagata attaaaatga taaccatctc gcaaataaat   4440
aagtatttta ctgttttcgt aacagttttg taataaaaaa acctataaat attccggatt   4500
attcataccg tcccaccatc gggcgcggat cctcgagatg ggtaaccatc atcatcatca   4560
tcacggagaa agcttgttta agggaccacg tgattacaac ccgatatcga gcaccatttg   4620
tcatttgacg aatgaatctg atgggcacac aacatcgttg tatggtattg gatttggtcc   4680
cttcatcatt acaaacaagc acttgtttag aagaaataat ggaacactgt tggtccaatc   4740
actacatggt gtattcaagg tcaagaacac cacgactttg caacaacacc tcattgatgg   4800
gagggacatg ataattattc gcatgcctaa ggatttccca ccatttcctc aaaagctgaa   4860
atttagagag ccacaaaggg aagagcgcat atgtcttgtg acaaccaact tccaaactaa   4920
gagcatgtct agcatggtgt cagacactag ttgcacattc ccttcatctg atggcatatt   4980
ctggaagcat tggattcaaa ccaaggatgg gcagtgtggc agtccattag tatcaactag   5040
agatgggttc attgttggta tacactcagc atcgaatttc accaacacaa acaattattt   5100
cacaagcgtg ccgaaaaact tcatggaatt gttgacaaat caggaggcgc agcagtgggt   5160
tagtggttgg cgattaaatg ctgactcagt attgtggggg ggccataaag ttttcatgag   5220
caaacctgaa gagccttttc agccagttaa ggaagcgact caactcatga atgaattggt   5280
gtactcgcaa ggtggtggtg aaaacctgta cttccagggt aaccacgctg aggagaagaa   5340
gctgaagctt agcaacactg tgctgccctc ggagtccatg aaggtggtgg ctgaatccat   5400
gggcatcgcc cagattcagg aggagacctg ccagctgcta acggatgagg tcagctaccg   5460
catcaaagag atcgcacagg atgccttgaa gttcatgcac atggggaagc ggcagaagct   5520
caccaccagt gacattgact acgccttgaa gctaaagaat gtcgagccac tctatggctt   5580
```

```
ccacgcccag gagttcattc ctttccgctt cgcctctggt gggggccggg agctttactt   5640
ctatgaggag aaggaggttg atctgagcga catcatcaat acccctctgc cccgggtgcc   5700
cctggacgtc tgcctcaaag ctcattggct gagcatcgag ggctgccagc cagctatccc   5760
cgagaacccg cccccagctc ccaaagagca acagaaggct gaagccacag aacccctgaa   5820
gtcagccaag ccaggccagg aggaagacgg acccctgaag ggcaaaggtc aaggggccac   5880
cacagccgac ggcaaaggga aagagaagaa ggcgccgccc ttgctggagg gggccccctt   5940
gcgactgaag ccccggagca tccacgagtt gtctgtggag cagcagctct actacaagga   6000
gatcaccgag gcctgcgtgg gctcctgcga ggccaagagg gcggaagccc tgcaaagcat   6060
tgccacggac cctggactgt atcagatgct gccacggttc agtaccttta tctcggaggg   6120
ggtccgtgtg aacgtggttc agaacaacct ggccctactc atctacctga tgcgtatggt   6180
gaaagcgctg atggacaacc ccacgctcta tctagaaaaa tacgtccatg agctgattcc   6240
agctgtgatg acctgcatcg tgagcagaca gttgtgcctg cgaccagatg tggacaatca   6300
ctgggcactc cgagactttg ctgcccgcct ggtggcccag atctgcaagc attttagcac   6360
aaccactaac aacatccagt cccggatcac caagaccttc accaagagct gggtggacga   6420
gaagacgccc tggacgactc gttatggctc catcgcaggc ttggctgagc tgggacacga   6480
tgttatcaag actctgattc tgccccggct gcagcaggaa ggggagcgga tccgcagtgt   6540
gctggacggc cctgtgctga gcaacattga ccggattgga gcagaccatg tgcagagcct   6600
cctgctgaaa cactgtgctc ctgttctggc aaagctgcgc ccaccgcctg acaatcagga   6660
cgcctatcgg gcagaattcg ggtcccttgg gcccctcctc tgctcccagg tggtcaaggc   6720
tcgggcccag gctgctctgc aggctcagca ggtcaacagg accactctga ccatcacgca   6780
gccccggccc acgctgaccc tctcgcaggc cccacagcct ggccctcgca cccctggctt   6840
gctgaaggtt cctggctcca tcgcacttcc tgtccagaca ctggtgtctg cacgagcggc   6900
tgccccacca cagccttccc ctcctccaac caagtttatt gtaatgtcat cgtcctccag   6960
cgccccatcc acccagcagg tcctgtccct cagcacctcg gcccccggct caggttccac   7020
caccacttcg cccgtcacca ccaccgtccc cagcgtgcag cccatcgtca agttggtctc   7080
caccgccacc accgcacccc ccagcactgc tccctctggt cctgggagtg tccagaagta   7140
catcgtggtc tcacttcccc caacagggga gggcaaagga ggccccacct cccatccttc   7200
tccagttcct cccccggcat cgtccccgtc cccactcagc ggcagtgccc tttgtggggg   7260
gaagcaggag gctggggaca gtccccctcc agctccaggg actccaaaag ccaatggctc   7320
ccagcccaac tccggctccc ctcagcctgc tccgcggtcc ggtggtggtg gtgaaaacct   7380
gtattttcag ggcgagtctg gcaagacggc ttctcccaag agcatgccga aagatgcaca   7440
gatgatggca caaatcctga aggatatggg gattacagaa tatgagccaa gagttataaa   7500
tcagatgttg gagtttgcct tccgatatgt gaccacaatt ctagatgatg caaaaattta   7560
ttcaagccat gctaagaaag ctactgttga tgcagatgat gtgcgattgg caatccagtg   7620
ccgcgctgat cagtctttta cctctcctcc cccaagagat tttttattag atattgcaag   7680
gcaaagaaat caaacccctt tgccattgat caagccatat tcaggtccaa ggttgccacc   7740
tgatagatac tgcttaacag ctccaaacta taggctgaaa tctttacaga aaaaggcatc   7800
aacttctgcg ggaagaataa cagtcccgcg gttaagtgtt ggttcagtta ctagcagacc   7860
aagtactccc acactaggca caccaacccc acagaccatg tctgtttcaa ctaaagtagg   7920
```

-continued

```
gactcccatg tccctcacag gtcaaaggtt tacagtacag atgcctactt ctcagtctcc   7980

agctgtaaaa gcttcaattc ctgcaacctc agcagttcag aatgttctga ttaatccatc   8040

attaatcggg tccaaaaaca ttcttattac cactaatatg atgtcatcac aaaatactgc   8100

caatgaatca tcaaatgcat tgaaaagaaa acgtgaagat gatgatgatg acgatgatga   8160

tgatgatgac tatgataatc tgcggtccgg ccaccatcat caccaccatt gataagctag   8220

cggccgcttt cgaatctaga gcctgcagtc tcgacaagct tgtcgagaag tactagagga   8280

tcataatcag ccataccaca tttgtagagg ttttacttgc tttaaaaaac ctcccacacc   8340

tccccctgaa cctgaaacat aaaatgaatg caattgttgt tgttaacttg tttattgcag   8400

cttataatgg ttacaaataa agcaatagca tcacaaattt cacaaataaa gcattttttt   8460

cactgcattc tagttgtggt ttgtccaaac tcatcaatgt atcttatcat gtctggatct   8520

gatcactgct tgagcctagg agatccgaac cagataagtg aaatctagtt ccaaactatt   8580

ttgtcatttt taattttcgt attagcttac gacgctacac ccagttccca tctattttgt   8640

cactcttccc taaataatcc ttaaaaactc catttccacc cctcccagtt cccaacgcca   8700

actccatgtg acaaaccgtc atcttcggct acttt                              8735
```